United States Patent
Shai et al.

(10) Patent No.: US 8,986,712 B2
(45) Date of Patent: Mar. 24, 2015

(54) PEPTIDES DERIVED FROM HIV-1 GP41 TRANSMEMBRANE DOMAIN FOR T-IMMUNOMODULATION

(75) Inventors: Yechiel Shai, Yahud (IL); Irun R. Cohen, Rehovot (IL); Tomer Cohen, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 13/512,556

(22) PCT Filed: Nov. 29, 2010

(86) PCT No.: PCT/IL2010/000995
§ 371 (c)(1),
(2), (4) Date: Sep. 4, 2012

(87) PCT Pub. No.: WO2011/064779
PCT Pub. Date: Jun. 3, 2011

(65) Prior Publication Data
US 2012/0321668 A1  Dec. 20, 2012

Related U.S. Application Data

(60) Provisional application No. 61/264,805, filed on Nov. 29, 2009.

(51) Int. Cl.
| | | |
|---|---|---|
| *A61K 39/21* | (2006.01) |
| *A61K 38/08* | (2006.01) |
| *A61K 38/04* | (2006.01) |
| *A61K 38/10* | (2006.01) |
| *A61K 38/16* | (2006.01) |
| *C07K 14/005* | (2006.01) |
| *A61P 11/00* | (2006.01) |
| *A61P 37/02* | (2006.01) |
| *A61P 37/08* | (2006.01) |

(52) U.S. Cl.
CPC ..... *C07K 14/005* (2013.01); *C12N 2740/16122* (2013.01)
USPC ........ 424/281.1; 530/324; 530/325; 530/326; 530/327; 530/328; 514/3.8; 424/188.1

(58) Field of Classification Search
CPC .............. A61K 39/145; C07K 14/005; C12N 2760/16134; C12N 2760/16121; C12N 2760/16122
See application file for complete search history.

(56) References Cited

U.S. PATENT DOCUMENTS

| | | | |
|---|---|---|---|
| 5,230,887 A | 7/1993 | Hoffmann |
| 5,556,744 A | 9/1996 | Weiner |
| 5,756,666 A | 5/1998 | Takiguchi |
| 5,981,706 A | 11/1999 | Wallen |
| 2003/0185822 A1 | 10/2003 | Gray |

FOREIGN PATENT DOCUMENTS

| | | | |
|---|---|---|---|
| WO | WO 9420127 A1 * | 9/1994 | ............ A61K 37/02 |
| WO | 2005/060350 A1 | 7/2005 | |
| WO | 2006/038131 A1 | 4/2006 | |
| WO | WO 2006038131 A2 * | 4/2006 | |
| WO | 2006/077601 A1 | 7/2006 | |
| WO | 2007/034489 A1 | 3/2007 | |
| WO | 2007/034490 A1 | 3/2007 | |
| WO | 2010/017209 A1 | 2/2010 | |
| WO | 2010/037402 A1 | 4/2010 | |

OTHER PUBLICATIONS

Roberts et al. Prediction of HIV Peptide Epitopes by a Novel Algorithm. AIDS Research and Human Retroviruses 1996, vol. 12, No. 7, p. 593-610.*

Avrahami et al. Bestowing Antifungal and Antibacterial Activities by Lipophilic Acid Conjugation to D,L-Amino Acid-Containing Antimicrobial Peptides: A Plausible Mode of Action. Biochemistry 2003, vol. 42, pp. 14946-14956.*

Bloch et al., (2007) T-cell inactivation and immunosuppressive activity induced by HIV gp41 via novel interacting motif. FASEB J 21(2): 393-401.

Cohen, Tomer et al., "Characterization of the interacting domain of the HIV-1 fusion peptide with the transmembrane domain of the T-cell receptor", Biochemistry, 47(16):4826-4833 (2008).

Cohen, Tomer et al., "HIV-1 gp41 and TCRalpha trans-membrane domains share a motif exploited by the HIV virus to modulate T-cell proliferation", PLoS Pathog, 6(9):e1001085 (2010).

Gallo, Stephen A. et al., "The HIV Env-mediated fusion reaction", Biochim Biophys Acta, 1614(1):36-50 (2003).

Gerber, Doron and Shai, Yechiel, "Insertion and organization within membranes of the delta-endotoxin pore-forming domain, helix 4-loop-helix 5, and inhibition of its activity by a mutant helix 4 peptide", J Biol Chem, 275(31):23602-23607 (2000).

Helseth, Eirik et al., "Changes in the transmembrane region of the human immunodeficiency virus type 1 gp41 envelope glycoprotein affect membrane fusion", J. Virol., 64 (12): 6314-6318 (1990).

Herrmann, Jana R. et al., "Complex patterns of histidine, hydroxylated amino acids and the GxxxG motif mediate high-affinity transmembrane domain interactions", J Mol Biol, 385(3):912-923 (2009).

Hochberg, Yosef Benjamini, Yoav, "More powerful procedures for multiple significance testing", Stat Med, 9(7):811-818 (1990).

Kaleeba, J. A. R. et al., "The OX-40 receptor provides a potent co-stimulatory signal capable of inducing encephalitogenicity in myelin-specific CD4+ T cells", Int Immunol, 10(4):453-461 (1998).

(Continued)

*Primary Examiner* — Louise Humphrey
(74) *Attorney, Agent, or Firm* — Rodney J. Fuller; Booth Udall Fuller, PLC

(57) ABSTRACT

The present invention relates to peptides, derivatives and analogs comprising an amino acid sequence derived from the transmembrane domain of HIV gp41 protein, pharmaceutical compositions comprising same, and uses thereof for therapy of inflammatory diseases and disorders, such as T-cell and/or monocyte mediated diseases.

13 Claims, 12 Drawing Sheets

(56) References Cited

OTHER PUBLICATIONS

Keppler, Oliver T. et al., "Modulation of specific surface receptors and activation sensitization in primary resting CD4+ T lymphocytes by the Nef protein of HIV-1", J Leukoc Biol, 79(3):616-627 (2006).

Kim, Jong Hwa et al., "Molecular dynamics studies of the transmembrane domain of gp41 from HIV-1", Biochim Biophys Acta, 1788(9):1804-1812 (2009).

Kliger, Yossef et al., "Fusion peptides derived from the HIV type 1 glycoprotein 41 associate within phospholipid membranes and inhibit cell-cell Fusion. Structure-function study", J Biol Chem, 272(21):13496-13505 (1997).

Manolios, Nicholas et al., "T-cell antigen receptor transmembrane peptides modulate T-cell function and T cell-mediated disease", Nat Med, 3(1):84-88 (1997).

Mocellin, Simone and Nitti, Donato, "TNF and cancer: the two sides of the coin", Front Biosci, 13:2774-2783 (abstract) (2008).

Needleman, Saul B. and Wunsch, Christian D., "A general method applicable to the search for similarities in the amino acid sequence of two proteins", J Mol Biol, 48(3):443-453 (1970).

Owens, Randall J. et al., "Mutations in the membrane-spanning domain of the human immunodeficiency virus envelope glycoprotein that affect fusion activity", J Virol, 68(1):570-574 (1994).

Pearson, William R. and Lipman, David J., "Improved tools for biological sequence comparison", Proc Natl Acad Sci USA, 85(8):2444-2448 (1988).

Quintana, Francisco J. et al., "HIV-1 fusion peptide targets the TCR and inhibits antigen-specific T cell activation", J Clin Invest, 115(8):2149-2158 (2005).

Ruegg, C. L. et al., "Identification, using synthetic peptides, of the minimum amino acid sequence from the retroviral transmembrane protein p15E required for inhibition of lymphoproliferation and its similarity to gp21 of human T-lymphotropic virus types I and II", J Virol, 63(8):3250-3256 (1989).

Ruegg, C. L. et al., "Inhibition of lymphoproliferation by a synthetic peptide with sequence identity to gp41 of human immunodeficiency virus type V", J Virol, 63(8):3257-3260 (1989).

Srinivasan, Sowmyalakshmi et al., "Inhibiting TNF-mediated signaling: a novel therapeutic paradigm for androgen independent prostate cancer", Apoptosis,15(2):153-161 (Feb. 2010).

Wang, Xin M. et al., "T-cell antigen receptor peptides inhibit signal transduction within the membrane bilayer", Clin Immunol, 105(2):199-207 (2002).

* cited by examiner

TCRα CP     GLRILLLKV     SEQ ID NO: 9

|||||::.|

SIV gp41 TMD     GLRILMFIV     SEQ ID NO: 8

Figure 2A

TCRα CP     GLRILLLKV     SEQ ID NO: 9

||||::..:

HIV-1 gp41 TMD     GLRIVFAVL     SEQ ID NO: 4

Figure 2B

SEQUENCE LISTING

```
<160> NUMBER OF SEQ ID NOS: 39

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Gly or Leu
<220> FEATURE:
<221> NAME/KEY: MISC_FEATURE
<222> LOCATION: (3)..(3)
<223> OTHER INFORMATION: Xaa = Val or Leu
<220> FEATURE:
<221> NAME/KEY: MISC_FEATURE
<222> LOCATION: (4)..(4)
<223> OTHER INFORMATION: Xaa = Gly or Val
<220> FEATURE:
<221> NAME/KEY: MISC_FEATURE
<222> LOCATION: (6)..(6)
<223> OTHER INFORMATION: Xaa = Arg or Glu

<400> SEQUENCE: 1

Gly Xaa Xaa Xaa Leu Xaa Ile Val Phe
1               5

<210> SEQ ID NO 2
<211> LENGTH: 22
<212> TYPE: PRT
<213> ORGANISM: Artificial Sequence
<220> FEATURE:
<223> OTHER INFORMATION: Synthetic peptide

<400> SEQUENCE: 2

Leu Phe Ile Met Ile Val Gly Gly Leu Val Gly Leu Arg Ile Val Phe
1               5                   10                  15

Ala Val Leu Ser Ile Val
            20

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide

<400> SEQUENCE: 3
```

Ile Val Gly Gly Leu Val Gly Leu Arg Ile Val Phe Ala Val Leu
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetic peptide

<400> SEQUENCE: 4

Ile Val Gly Gly Leu Val Gly Leu Arg Ile Val Phe Ala Val
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic peptide

<400> SEQUENCE: 5

Ile Val Gly Gly Leu Val Glu Leu Arg Ile Val Phe Ala Val
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gly Leu Val Gly Leu Arg Ile Val Phe
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic peptide

<400> SEQUENCE: 7

Ile Val Gly Gly Gly Leu Val Leu Arg Ile Val Phe Ala Val
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Gly Leu Arg Ile Val Phe Ala Val
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

```
Gly Leu Arg Ile Val Phe Ala Val Leu
1               5

<210> SEQ ID NO 10
<211> LENGTH: 27
<212> TYPE: PRT
<213> ORGANISM: Artificial Sequence
<220> FEATURE:
<223> OTHER INFORMATION: Synthetic peptide

<400> SEQUENCE: 10

Lys Lys Lys Leu Phe Ile Met Ile Val Gly Gly Leu Val Gly Leu Arg
1               5                   10                  15

Ile Val Phe Ala Val Leu Ser Ile Lys Lys Lys
            20                  25

<210> SEQ ID NO 11
<211> LENGTH: 22
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: D-Val
<220> FEATURE:
<221> NAME/KEY: MISC_FEATURE
<222> LOCATION: (13)..(13)
<223> OTHER INFORMATION: D-Leu

<400> SEQUENCE: 11

Leu Phe Ile Met Ile Val Gly Gly Leu Val Gly Leu Arg Ile Val Phe
1               5                   10                  15

Ala Val Leu Ser Ile Val
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-Val
<220> FEATURE:
<221> NAME/KEY: MISC_FEATURE
<222> LOCATION: (6)..(6)
<223> OTHER INFORMATION: D-Val
<220> FEATURE:
<221> NAME/KEY: MISC_FEATURE
<222> LOCATION: (9)..(9)
<223> OTHER INFORMATION: D-Arg
<220> FEATURE:
<221> NAME/KEY: MISC_FEATURE
<222> LOCATION: (14)..(14)
<223> OTHER INFORMATION: D-Val

<400> SEQUENCE: 12

Ile Val Gly Gly Leu Val Gly Leu Arg Ile Val Phe Ala Val Leu
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (12)..(12)
<223> OTHER INFORMATION: D-Phe

<400> SEQUENCE: 13

Ile Val Gly Gly Gly Leu Val Leu Arg Ile Val Phe Ala Val
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: D-Arg

<400> SEQUENCE: 14

Ile Val Gly Gly Gly Leu Val Leu Arg Ile Val Phe Ala Val
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: D-Val
<220> FEATURE:
<221> NAME/KEY: MISC_FEATURE
<222> LOCATION: (11)..(11)
<223> OTHER INFORMATION: D-Val

<400> SEQUENCE: 15

Ile Val Gly Gly Gly Leu Val Leu Arg Ile Val Phe Ala Val
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (9)..(9)
<223> OTHER INFORMATION: D-Glu
<220> FEATURE:
<221> NAME/KEY: MISC_FEATURE
<222> LOCATION: (13)..(13)
<223> OTHER INFORMATION: D-Ala

<400> SEQUENCE: 16

Ile Val Gly Gly Leu Val Gly Leu Glu Ile Val Phe Ala Val
1               5                   10

<210> SEQ ID NO 17
```

```
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (6)..(6)
<223> OTHER INFORMATION: D-Arg

<400> SEQUENCE: 17

Gly Leu Val Gly Leu Arg Ile Val Phe
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (8)..(8)
<223> OTHER INFORMATION: D-Val

<400> SEQUENCE: 18

Gly Leu Val Gly Leu Arg Ile Val Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: D-Val

<400> SEQUENCE: 19

Gly Leu Arg Ile Val Phe Ala Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: D-Phe

<400> SEQUENCE: 20

Gly Leu Arg Ile Val Phe Ala Val
1               5
```

```
<210> SEQ ID NO 21
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (7)..(7)
<223> OTHER INFORMATION: D-Ala

<400> SEQUENCE: 21

Gly Leu Arg Ile Val Phe Ala Val Leu
1               5

<210> SEQ ID NO 22
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Undecanoic acid coupled to the N-terminus

<400> SEQUENCE: 22

Ile Val Gly Gly Gly Leu Val Leu Arg Ile Val Phe Ala Val
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: D-Val
<220> FEATURE:
<221> NAME/KEY: MISC_FEATURE
<222> LOCATION: (11)..(11)
<223> OTHER INFORMATION: D-Val
<220> FEATURE:
<221> NAME/KEY: MOD_RES
<222> LOCATION: (14)..(14)
<223> OTHER INFORMATION: Undecanoic acid coupled to the C-terminus
<220> FEATURE:
<221> NAME/KEY: MISC_FEATURE
<222> LOCATION: (14)..(14)
<223> OTHER INFORMATION: D-Val

<400> SEQUENCE: 23

Ile Val Gly Gly Gly Leu Val Leu Arg Ile Val Phe Ala Val
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Cholesterol coupled to the N-terminus
<220> FEATURE:
<221> NAME/KEY: MISC_FEATURE
```

-continued

```
<222> LOCATION: (7)..(7)
<223> OTHER INFORMATION: D-Val
<220> FEATURE:
<221> NAME/KEY: MISC_FEATURE
<222> LOCATION: (11)..(11)
<223> OTHER INFORMATION: D-Val
<220> FEATURE:
<221> NAME/KEY: MISC_FEATURE
<222> LOCATION: (14)..(14)
<223> OTHER INFORMATION: D-Val

<400> SEQUENCE: 24

Ile Val Gly Gly Gly Leu Val Leu Arg Ile Val Phe Ala Val
 1               5                  10

<210> SEQ ID NO 25
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: D-Val
<220> FEATURE:
<221> NAME/KEY: MISC_FEATURE
<222> LOCATION: (11)..(11)
<223> OTHER INFORMATION: D-Val
<220> FEATURE:
<221> NAME/KEY: MOD_RES
<222> LOCATION: (14)..(14)
<223> OTHER INFORMATION: Cholesterol coupled to the C-terminus
<220> FEATURE:
<221> NAME/KEY: MISC_FEATURE
<222> LOCATION: (14)..(14)
<223> OTHER INFORMATION: D-Val

<400> SEQUENCE: 25

Ile Val Gly Gly Gly Leu Val Leu Arg Ile Val Phe Ala Val
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Vitamin E coupled to the N-terminus
<220> FEATURE:
<221> NAME/KEY: MISC_FEATURE
<222> LOCATION: (7)..(7)
<223> OTHER INFORMATION: D-Val
<220> FEATURE:
<221> NAME/KEY: MISC_FEATURE
<222> LOCATION: (11)..(11)
<223> OTHER INFORMATION: D-Val
<220> FEATURE:
<221> NAME/KEY: MISC_FEATURE
<222> LOCATION: (14)..(14)
<223> OTHER INFORMATION: D-Val

<400> SEQUENCE: 26

Ile Val Gly Gly Gly Leu Val Leu Arg Ile Val Phe Ala Val
 1               5                  10

<210> SEQ ID NO 27
<211> LENGTH: 14
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Octanoic acid copuled to the N-terminus
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (9)..(9)
<223> OTHER INFORMATION: D-Glu
<220> FEATURE:
<221> NAME/KEY: MISC_FEATURE
<222> LOCATION: (13)..(13)
<223> OTHER INFORMATION: D-Ala

<400> SEQUENCE: 27

Ile Val Gly Gly Leu Val Gly Leu Glu Ile Val Phe Ala Val
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Octanoic acid copuled to the N-terminus
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (6)..(6)
<223> OTHER INFORMATION: D-Arg

<400> SEQUENCE: 28

Gly Leu Val Gly Leu Arg Ile Val Phe
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Vitamin E copuled to the N-terminus
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (6)..(6)
<223> OTHER INFORMATION: D-Arg
<220> FEATURE:
<221> NAME/KEY: MISC_FEATURE
<222> LOCATION: (8)..(8)
<223> OTHER INFORMATION: D-Val

<400> SEQUENCE: 29

Gly Leu Val Gly Leu Arg Ile Val Phe
1               5
```

```
<210> SEQ ID NO 30
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Cholesterol copuled to the N-terminus
<220> FEATURE:
<221> NAME/KEY: MISC_FEATURE
<222> LOCATION: (3)..(3)
<223> OTHER INFORMATION: D-Arg

<400> SEQUENCE: 30

Gly Leu Arg Ile Val Phe Ala Val
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: D-Phe
<220> FEATURE:
<221> NAME/KEY: MOD_RES
<222> LOCATION: (8)..(8)
<223> OTHER INFORMATION: Cholesterol copuled to the C-terminus

<400> SEQUENCE: 31

Gly Leu Arg Ile Val Phe Ala Val
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: Cholesterol copuled to the C-terminus

<400> SEQUENCE: 32

Gly Leu Arg Ile Val Phe Ala Val
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: D-Phe
<220> FEATURE:
<221> NAME/KEY: MOD_RES
<222> LOCATION: (8)..(8)
<223> OTHER INFORMATION: Myristic acid copuled to the C-terminus

<400> SEQUENCE: 33

Gly Leu Arg Ile Val Phe Ala Val
1               5
```

<210> SEQ ID NO 34
<211> LENGTH: 5
<212> TYPE: PRT
<213> ORGANISM: Artificial Sequence
<220> FEATURE:
<223> OTHER INFORMATION: Synthetic peptide

<400> SEQUENCE: 34

Leu Arg Ile Val Phe
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic peptide

<400> SEQUENCE: 35

Leu Glu Ile Val Phe
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa = Arg or Glu

<400> SEQUENCE: 36

Leu Xaa Ile Val Phe
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic peptide

<400> SEQUENCE: 37

Gly Leu Arg Ile Leu Leu Leu Lys Val
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic peptide

<400> SEQUENCE: 38

Gly Leu Arg Ile Leu Met Phe Ile Val
1               5

<210> SEQ ID NO 39
<211> LENGTH: 16
<212> TYPE: PRT
<213> ORGANISM: Artificial Sequence

```
<220> FEATURE:
<223> OTHER INFORMATION: Synthetic peptide

<400> SEQUENCE: 39

Met Val Leu Gly Val Phe Ala Leu Leu Pro Leu Ile Ser Gly Ser Leu
1               5                   10                  15
```

PEPTIDES DERIVED FROM HIV-1 GP41 TRANSMEMBRANE DOMAIN FOR T-IMMUNOMODULATION

RELATED APPLICATION DATA

This application is the U.S. National Stage of International Application No. PCT/IL2010/000995, filed Nov. 29, 2010, which claims the benefit of U.S. Provisional Application No. 61/264,805, filed Nov. 29, 2009, the contents of each of which are herein expressly incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 12,953 byte ASCII (text) file named "Seq_List" created on May 28, 2012.

FIELD OF THE INVENTION

The present invention relates to peptides and derivatives or analogs including lipopeptides, comprising an amino acid sequence derived from the transmembrane domain of HIV gp41 protein, pharmaceutical compositions comprising same, and uses thereof. The peptides and compositions of the invention are particularly useful for treating T-cell mediated diseases and disorders, such as inflammatory and autoimmune diseases, and for treating conditions associated with monocyte activation and/or TNF-α secretion.

BACKGROUND OF THE INVENTION

Human immunodeficiency virus (HIV) infection confounds the immune response. Untreated HIV infection usually leads to a state of general immunosuppression, the acquired immune deficiency syndrome (AIDS), and susceptibility to otherwise innocuous opportunistic infections. However, to establish a successful infection and replicate, the virus has to evade immune control, a task that HIV accomplishes by using a broad array of mechanisms.

HIV, like other enveloped viruses, requires a fusion of the viral membrane with the host cellular membrane in order to enter and infect target cells. For that purpose it employs a fusion protein, the transmembrane glycoprotein gp41, which is non-covalently linked to the surface glycoprotein gp120. Together, gp120 and gp41 form the envelope glycoprotein complex which is embedded in the viral membrane as a trimer. The surface gp120 is primarily involved in recognition of cellular receptors, whereas gp41 is anchored to the viral membrane and mediates membrane fusion.

The gp41 Protein

The gp41 protein is composed of cytoplasmic, transmembrane, and extracellular domains (Chan et al., Biochim. Biophys. Acta. 1614, 36-50, 2003). The extracellular domain (ectodomain) contains four major functional regions: closest to the viral membrane is the tryptophan-rich membrane proximal ectodomain region, followed by a C-terminal heptad repeat, an N-terminal heptad repeat, and a stretch of 16 hydrophobic residues, located in the N terminus, termed fusion peptide (FP) (FIG. 1). During the initial step of the membrane fusion process, FP anchors gp41 to the target membrane. In the next step, the gp41 heptad repeat domains interact with each other to form a six-helix bundle conformation and bridge the gap between the opposing membranes and eventually complete the fusion process.

International Patent Application No. WO 2005/060350 of one of the inventors of the present invention, discloses membrane binding diastereomeric peptides comprising amino acid sequences corresponding to a fragment of a transmembrane protein, having at least two amino acid residues of the diastereomeric peptides in a D-isomer configuration, useful in inhibiting fusion membrane protein events, including specifically viral replication and transmission. WO 2005/060350 discloses, inter alia, the use of diastereomeric peptides corresponding to amino acids 512 to 544 of HIV-1 gp41 and to amino acids 638 to 673 of HIV-1$_{LAV}$gp41 for inhibiting membrane fusion processes.

In addition to its role in mediating the actual fusion event, gp41 has been shown to contain two immunosuppressive regions that are believed to suppress the HIV-specific immunity. The first is the above mentioned N terminus hydrophobic region known as the fusion peptide (FP) (Quintana et al., 2005, J. Clin. Invest. 115, 2149-2158; Cohen, 2008, Biochemistry 47, 4826-4833) and the second is the 583-599 region known as immunosuppressive peptide (ISU) (Ruegg et al., 1989, J. Virol. 63, 3257-3260). Interestingly, the mechanisms by which these two immunosuppressive peptides exert their activity are different. The FP inhibits antigen-specific T-cell proliferation by specifically interacting with the T-cell receptor α subunit (TCRα), whereas the ISU inhibits T-cell proliferation induced by anti-CD3 antibodies or by Phorbol Myristate Acetate (PMA)/ionomycin (Ruegg et al., 1989, J. Virol. 63, 3250-3256).

International Patent Application No. WO 2006/077601, to some of the inventors of the present application, provides peptides derived from the HIV gp41 FP domain useful for prevention or treatment of autoimmune and other T cell-mediated pathologies. WO 2006/077601 further provides novel peptides derived from the HIV gp41 FP domain.

International Patent Application No. WO 2010/017209, published after the priority date of the present application, discloses isolated immunogens including variant hepatitis B surface antigens (HBsAgs) wherein the transmembrane domain of the HBsAg is replaced with a gp41 antigenic insert. Particularly, the antigenic insert includes an antigenic polypeptide fragment of gp41 including the membrane proximal region of gp41 and a transmembrane region of gp41. According to the '209 application, the variant HBsAgs may be used for inducing an immune response to HIV-1.

Mutations in the membrane spanning domain of the HIV envelope glycoprotein were shown to affect fusion activity (Owens et al., J. Virol. 68 (1): 570-574, 1994; Helseth et al., J. Virol. 64 (12): 6314-6318, 1990). Recently, Kim et al. studied gp41 transmembrane domain stability in different environments (lipid or water) via mutating glycine 691, 695 and arginine 697 (Kim et al., Biochimica et Biophysica Acta 1788, 2009, 1804-12).

U.S. Pat. No. 5,756,666 provides peptides capable of inducing immune response to HIV, the peptides being fragments of HIV having a sequence of 8 to 11 amino acid residues corresponding to an HLA-binding motif, wherein said peptides bind to HLA and induce killer cells capable of attacking HIV-infected cells as target cells.

U.S. Pat. No. 5,556,744 provides a panel of HIV peptides derived from gp120 and gp41, pharmaceutical and vaccine compositions containing same useful in diagnosing whether or not a patient is of vertical HIV transmission status, methods for diagnosing same and methods for identifying epitopes and peptides associated with non-transmission status. U.S. Pat. No. 5,981,706 is directed to methods for synthesizing heat shock protein (HSP)-peptide complexes comprising the steps of adding a shock protein to a denatured protein matrix to bind the HSP to the denatured protein matrix; and adding a complexing solution comprising a peptide to elute a HSP-peptide complex. The '706 publication further provides the HSP-peptide complexes and an apparatus for synthesizing said complexes. Among the peptides suitable for use as complexing agents, according to the '706 publication, are gp41 derived peptides.

T Cells

The activity of T cells is regulated by antigen, presented to a T cell in the context of a major histocompatibility complex (MHC) molecule. The T cell receptor (TCR) then binds to the MHC-peptide complex. Once antigen is complexed to MHC, the MHC-antigen complex is bound by a specific TCR on a T cell, thereby altering the activity of that T cell. The TCR complex is thus an attractive target for immunomodulation.

The TCR complex of the majority of the mature T cells is a TCRαβ heterodimer associated to the γ, β, ε and ζ chains of CD3. This complex is stabilized by interactions between the transmembrane domain of the TCR chains and CD3 subunits. The interaction of the TCR with a peptide presented by MHC induces a conformational change in the TCR that triggers CD3 phosphorylation.

While the normal immune system is closely regulated, aberrations in immune responses are not uncommon. In some instances, the immune system functions inappropriately and reacts to a component of the host as if it were, in fact, foreign. Such a response results in an autoimmune disease, in which the host's immune system attacks the host's own tissue. T cells, directly or indirectly affect such autoimmune pathologies.

Numerous diseases are believed to result from autoimmune mechanisms. Prominent among these are rheumatoid arthritis, systemic lupus erythematosus, multiple sclerosis, Type I diabetes, myasthenia gravis, pemphigus vulgaris. Autoimmune diseases affect millions of individuals worldwide and the cost of these diseases, in terms of actual treatment expenditures and lost productivity, is measured in billions of dollars annually.

T cells also play a major role in the rejection for organ transplantation or graft versus host disease by bone marrow (hematopoietic stem cell) transplantation. Regulation of such immune responses is therefore therapeutically desired.

Traditional reagents and methods used to attempt to regulate an immune response in a patient result in unwanted side effects and limited effectiveness. For example, immunosuppressive reagents (e.g., cyclosporin A, azathioprine, and prednisone) used to treat patients with autoimmune diseases also suppress the patient's entire immune response, thereby increasing the risk of infection, and can cause toxic side effects to non-lymphoid tissues. Due to the medical importance of immune regulation and the inadequacies of existing immunopharmacological reagents, reagents and methods to regulate specific parts of the immune system have been the subject of study for many years.

A method of treating or inhibiting symptoms of an autoimmune disease by administering a sub-immunogenic amount of an antigen more immunoreactive with alloimmune-immunogen-absorbed (AIA) serum as compared to nonimmune serum of the same species was disclosed in U.S. Pat. No. 5,230,887. One putative antigen, based on its purported serological cross reactivity with MHC Class II antigens, was suggested to be intact gp41 of HIV. The alleged cross reactivity resides in a C-terminal peptide.

International Patent Application No. WO 2007/034489, to one of the inventors of the present application, provides immunogenic compositions comprising the T-Cell Receptor constant domain and peptides derived therefrom, effective in preventing or treating T cell mediated inflammatory disease. The immunogenic compositions of WO 2007/034489 comprise at least one immunogen selected from the group consisting of: (i) an isolated constant domain of a chain of a human TCR; and (ii) a peptide comprising an immunogenic fragment of the constant domain of a chain of a TCR.

International Patent Application No. WO 2007/034490 provides diastereomeric peptides and lipopeptides derived from the T cell receptor alpha (TCRα) transmembrane domain (TMD), pharmaceutical compositions comprising same, and uses thereof for therapy of T cell mediated inflammatory diseases.

Monocytes and Macrophages

Monocytes are critical effectors and regulators of the innate immune response, as well as in the adaptive immune response of vertebrate animals. Monocytes, and their differentiated cells, macrophages, are phagocyte cells which reside in various tissues and are among the first cells of any organ to be exposed to infectious agents and to become activated in response to an insult. Upon activation macrophages participate actively in the onset of inflammation by releasing cytokines that amplify the initial inflammatory response. Monocytes and macrophages are the prime immune cells managing inflammatory responses, which contribute to development of number of diseases and disorders such as cancer, sepsis, asthma and diabetes.

The Tumor Necrosis Factor (TNF) family of cytokines plays an essential role in multiple biological functions including inflammation, organogenesis, host defense, autoimmunity, and apoptosis. TNF-α is a central proinflammatory cytokine and plays an important role in various pathophysiological functions, being such as cell growth, differentiation and death. TNF appears not only to orchestrate acute responses to infection and immunological injury but also to act as a balancing factor required for the re-establishment of physiological homeostasis and regulation.

Despite the approval of TNF as an anticancer agent, it has been implicated in both cancer development and progression in some preclinical models. In particular, as a central mediator of inflammation, TNF might represent one of the molecular links between chronic inflammation and the subsequent development of malignant disease. Furthermore, deregulated TNF expression within the tumor microenvironment appears to favor malignant cell tissue invasion, migration and ultimately metastasis formation (Mocellin and Nitti, Front. Biosci. 2008 Jan. 1; 13:2774-85). Inhibition of TNF-α mediated signaling as means for treatment cancer has been recently disclosed. For instance, inhibition of TNF-mediated signaling was demonstrated as a potent therapeutic agent for prostate cancer (Srinivasan et al. Apoptosis. 2010 February; 15(2):153-61).

None of the background art, however, discloses or suggests that peptides derived from the transmembrane domain of HIV-1 gp41 regulate T cell and/or monocyte activation, and are particularly useful in treating or preventing diseases and disorders such as autoimmune diseases and inflammatory diseases.

There exists a long-felt need for more effective means of curing or ameliorating inflammatory or autoimmune diseases, such as pathologies associated with T cell activation and/or TNF-α secretion. In addition, there exists a long-felt need for curing or ameliorating TNF-α mediated pathology.

SUMMARY OF THE INVENTION

The present invention provides peptides, derivatives and analogs comprising an amino acid sequence derived from the HIV gp41 transmembrane domain and to pharmaceutical compositions comprising same effective in preventing or treating inflammatory disease or disorders. The peptides and compositions of the invention are particularly useful in treating pathologies associated with T cell activation and/or monocyte activation. Further, the peptides and compositions of the invention are useful in treating pathologies associated with TNF-α signaling.

The present invention is based, in part, on the unexpected discovery that the transmembrane domain (TMD) of HIV-1 gp41 (LFIMIVGGLVGLRIVFAVLSIV; SEQ ID NO: 1), fragments, analogs and derivatives thereof, have therapeutic anti-inflammatory properties. It is now disclosed for the first time that the transmembrane domain of gp41 co-localizes with the CD3/TCR complex of activated and resting T cells, and inhibits their proliferation. Unexpectedly, a peptide derived from the gp41 transmembrane domain (GLVGLRIVF; SEQ ID NO: 2) exhibited a remarkably higher inhibition of T-cell proliferation than did the full length transmembrane domain. Significantly, T cell activation was inhibited following activation by MOG 35-55, a peptide which is known to play a role in autoimmune diseases, in particular, multiple sclerosis.

It is further disclosed that the peptides of the present invention are useful in inhibiting TNF-α secretion from macrophage. Specifically, the peptides were shown to interfere with the response of Toll-like receptor-2 (TLR2) and TLR4 towards their respective ligands, Lipoteichoic acid (LTA) and Lipopolysaccharide (LPS).

These unexpected findings provide a novel function of gp41 TMD, and fragments or analogs derived from the gp41 TMD, useful as anti-inflammatory and immunosuppressive agents capable of selectively inhibiting the activation of T lymphocytes and/or macrophage secretion of TNF-α.

According to a first aspect, the present invention provides an isolated peptide of 9-30 amino acids, or an analog or derivative thereof, wherein the isolated peptide comprises the amino acid sequence of formula I (SEQ ID NO: 1):

$$Gly\text{-}X_1\text{-}X_2\text{-}X_3\text{-}Leu\text{-}X_4\text{-}Ile\text{-}Val\text{-}Phe \quad I$$

wherein $X_1$ is selected from the group consisting of a Leucine (Leu) and a Glycine (Gly) amino acid residue;

$X_2$ is selected from the group consisting of a Valine (Val) and a Leucine (Leu) amino acid residue;

$X_3$ is selected from the group consisting of a Glycine (Gly) and a Valine (Val) amino acid residue;

$X_4$ is selected from the group consisting of an Arginine (Arg) and a Glutamic acid (Glu) amino acid residue.

According to one embodiment, the isolated peptide comprises the sequence of general formula I, wherein $X_1$ is a Leucine, $X_2$ is a Valine and $X_3$ is a Glycine residue.

According to certain embodiments, the isolated peptide of general formula I is selected from the group consisting of:

```
                                        (SEQ ID NO: 6)
GLVGLRIVF,
                                        (SEQ ID NO: 4)
IVGGLVGLRIVFAV,
                                        (SEQ ID NO: 3)
IVGGLVGLRIVFAVL,
```

-continued

```
                                        (SEQ ID NO: 2)
LFIMIVGGLVGLRIVFAVLSIV,
and
                                        (SEQ ID NO: 5)
IVGGLVELRIVFAV.
```

Each possibility is a separate embodiment of the present invention.

According to another embodiment, the isolated peptide of general formula I comprises the amino acid sequence GLVGLRIVF (SEQ ID NO: 6). According to an exemplary embodiment, the isolated peptide of general formula I consists of the amino acid sequence GLVGLRIVF (SEQ ID NO: 6).

According to another embodiment, the isolated peptide comprises the sequence of general formula I, wherein $X_1$ is a Glycine, $X_2$ is a Leucine, $X_3$ is a Valine and $X_4$ is an Arginine residue. According to another embodiment, the isolated peptide comprises of the amino acid IVGGGLVLRIVFAV (SEQ ID NO: 7). According to one embodiment, the isolated peptide consists of the amino acid IVGGGLVLRIVFAV (SEQ ID NO: 7).

According to certain embodiments, the isolated peptide further comprises 1-4 basic amino acid residues (i.e., positively charged amino acids) contiguous to at least one of the peptide's termini. According to particular embodiments, the basic amino acid residue is independently selected from Lysine and Arginine residues. In one embodiment, the 1-4 basic amino acid residues are contiguous to the N-terminus of said peptide. In another embodiment, said 1-4 basic amino acid residues are contiguous to the C-terminus of said peptide. In an additional embodiment, said 1-4 basic amino acid residues are contiguous to the C-terminus and N-terminus of said peptide. In additional embodiments, the isolated peptide comprises 1, 2, 3 or 4 basic amino acid residues contiguous to at least one of the peptide's termini, wherein each possibility represents a separate embodiment of the present invention. According to one particular embodiment, the isolated peptide consists of the amino acid sequence KKKLFIMIVGGLVGLRIVFAVLSIVKKK (SEQ ID NO: 10).

According to another embodiment, the isolated peptide comprises at least one D amino acid. According to another embodiment, the isolated peptide comprises at least two D amino acids. According to another embodiment, the isolated peptide comprises three D amino acids. Each possibility represents a separate embodiment of the present invention.

According to particular embodiments, the analog is an amino acid sequence selected from SEQ ID NO: 2-SEQ ID NO: 7 and SEQ ID NO: 10, wherein said analog comprises at least one D amino acid. Each possibility represents a separate embodiment of the present invention.

According to another embodiment, the D amino acid is an amino acid selected from Valine, Leucine, Arginine, Glutamic acid, Alanine and Phenylalanine, wherein each possibility is a separate embodiment of the present invention.

According to some embodiments, the isolated peptide is selected from the group consisting of:

```
                                        (SEQ ID NO: 11)
LFIMIvGGLVGlRIVFAVLSIV,
                                        (SEQ ID NO: 12)
IvGGLvGLrIVFAvL,
                                        (SEQ ID NO: 13)
IVGGGlVLRIVfAV,
```

IVGGGLVLrIVFAV, (SEQ ID NO: 14)

IVGGGLvLRIvFAV, (SEQ ID NO: 15)

IVGGlVGLeIVFaV, (SEQ ID NO: 16)

GlVGLrIVF,
and (SEQ ID NO: 17)

GlvGLrIvF, (SEQ ID NO: 18)

wherein "v" denotes D-Val, "l" denotes D-Leu, "r" denotes D-Arg, "e" denotes D-Glu, "a" denotes D-Ala, and "f" denotes D-Phe, wherein each possibility is a separate embodiment of the present invention.

The isolated peptide of the invention may be conjugated or coupled to a hydrophobic moiety. In one embodiment, the present invention provides a lipophilic conjugate comprising the isolated peptide of the present invention, conjugated to a hydrophobic moiety. The hydrophobic moiety may be conjugated to the N-terminus or C-terminus of said peptide. Typically, the peptide coupled to a hydrophobic moiety (thus forming a lipophilic conjugate) maintains its capability of treating inflammatory disease or disorder, e.g., pathologies associated with activated or proliferated T cells and/or activated macrophages.

According to some embodiments, the hydrophobic moiety is selected from the group consisting of a fatty acid, a sterol and a vitamin (such as a fat soluble vitamin). According to another embodiment, the isolated peptide is conjugated a fatty acid. The fatty acid, in some embodiments, is selected from saturated, unsaturated, monounsaturated and polyunsaturated fatty acids, wherein each possibility represents a separate embodiment of the present invention. According to another embodiment, the fatty acid has at least six carbon atoms. Non limiting examples of fatty acid conjugates are C6, C8, C10, C11, C12, C14, C16 and C18.

According to another embodiment, the fatty acid is selected from the group consisting of: octanoic acid, decanoic acid, undecanoic acid, dodecanoic acid, myristic acid, palmitic acid, stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, and cerebronic acid, wherein each possibility is a separate embodiment of the present invention.

According to particular embodiments, the fatty acid is selected from the group consisting of undecanoic acid, octanoic acid and myristic acid.

According to some embodiments, the hydrophobic moiety is a sterol. According to particular embodiments, the sterol is a cholesterol. According to additional embodiments the hydrophobic moiety is a fat soluble vitamin selected from the group consisting of vitamin A, vitamin D, vitamin E and vitamin K, wherein each possibility represents a separate embodiment of the present invention. According to one embodiment, the hydrophobic moiety is vitamin E.

According to some embodiments, the lipophilic conjugate (i.e., the isolated peptide conjugated to a hydrophobic moiety) is selected from the group consisting of:

Undecanoic acid-IVGGGLVLRIVFAV, (SEQ ID NO: 22)

IVGGGLvLRIvFAv-Undecanoic acid, (SEQ ID NO: 23)

Cholesterol-IVGGGLvLRIvFAv, (SEQ ID NO: 24)

IVGGGLvLRIvFAv-Cholesterol, (SEQ ID NO: 25)

Vitamin E-IVGGGLvLRIvFAv, (SEQ ID NO: 26)

Octanoic acid-IVGGlVGLeIVFaV, (SEQ ID NO: 27)

Octanoic acid-GlVGLrIVF,
and (SEQ ID NO: 28)

Vitamin E-GlvGLrIvF, (SEQ ID NO: 29)

wherein "v" denotes D-Val, "l" denotes D-Leu, "r" denotes D-Arg, "e" denotes D-Glu, "a" denotes D-Ala, and "f" denotes D-Phe, wherein each possibility is a separate embodiment of the present invention.

According to another aspect, the present invention provides a pharmaceutical composition comprising as an active ingredient an isolated peptide or a lipophilic conjugate of the present invention, and a pharmaceutically acceptable carrier. According to one embodiment, the pharmaceutical composition comprises the isolated peptide of the present invention.

In some embodiments, the isolated peptide consists of 9-30 amino acids comprising the amino acid sequence of G-$X_1$-$X_2$-$X_3$-L-$X_4$-I-V-F (SEQ ID NO: 1; formula I), wherein $X_1$ is selected from the group consisting of a Leucine and a Glycine amino acid residue; $X_2$ is selected from the group consisting of a Valine and a Leucine amino acid residue; $X_3$ is selected from the group consisting of a Glycine and a Valine amino acid residue; $X_4$ is selected from the group consisting of an Arginine and a Glutamic acid amino acid residue; or an analog or derivative thereof.

According to another embodiment, the pharmaceutical composition comprises an isolated peptide consisting of an amino acid sequence selected from SEQ ID NO: 2-SEQ ID NO: 6, wherein each possibility is a separate embodiment of the present invention. According to another embodiment, the pharmaceutical composition comprises an isolated peptide comprising the amino acid sequence GLVGLRIVF (SEQ ID NO: 6). According to an exemplary embodiment, the pharmaceutical composition comprises an isolated peptide consisting of the amino acid sequence GLVGLRIVF (SEQ ID NO: 6).

According to another embodiment, the pharmaceutical composition comprises the lipophilic conjugate of the present invention. According to another embodiment, the pharmaceutical composition comprises a lipophilic conjugate selected from the group consisting of: SEQ ID NO: 22-SEQ ID NO: 29, wherein each possibility is a separate embodiment of the present invention.

According to another aspect, the present invention provides a method of treating an inflammatory disease or disorder in a subject in need thereof, comprising administering to the subject a therapeutically effective amount of a pharmaceutical composition comprising a pharmaceutically acceptable carrier and as an active ingredient a lipophilic conjugate of the present invention or an isolated peptide of 9-30 amino acids comprising the amino acid sequence of general formula I: G-$X_1$-$X_2$-$X_3$-L-$X_4$-I-V-F (SEQ ID NO: 1), wherein $X_1$ is selected from the group consisting of a Leucine and a Glycine amino acid; residue; $X_2$ is selected from the group consisting of a Valine and a Leucine amino acid residue; $X_3$ is selected from the group consisting of a Glycine and a Valine amino acid residue; $X_4$ is selected from the group consisting of an Arginine and a Glutamic acid amino acid residue; or an analog or derivative thereof.

According to another aspect, the present invention provides a method of treating an inflammatory disease or disorder in a subject in need thereof, comprising administering to the subject a therapeutically effective amount of a pharmaceutical composition comprising an isolated peptide of 5-30 amino acids derived from the amino acid sequence LFIMIVGGLVGLRIVFAVLSIV (SEQ ID NO: 2), or an analog or derivative thereof.

According to another embodiment, the method comprises an isolated peptide comprising an amino acid sequence selected from L-$X_4$-I-V-F (SEQ ID NO: 36), wherein $X_4$ is selected from the group consisting of an Arginine and a Glutamic acid amino acid residue. According to another embodiment, the method comprises an isolated peptide comprising an amino acid sequence selected from LRIVF (SEQ ID NO: 34) or LEIVF (SEQ ID NO: 35). According to one embodiment, the method comprises an isolated peptide comprising the amino acid sequence LRIVF (SEQ ID NO: 34). According to another embodiment, the method comprises an isolated peptide comprising the amino acid sequence LEIVF (SEQ ID NO: 35).

According to some embodiments, the method comprises a peptide selected from the group consisting of:

```
                                (SEQ ID NO: 6)
GLVGLRIVF, (SEQ ID NO: 4)
IVGGLVGLRIVFAV, (SEQ ID NO: 3)
IVGGLVGLRIVFAVL, (SEQ ID NO: 2)
LFIMIVGGLVGLRIVFAVLSIV, (SEQ ID NO: 5)
IVGGLVELRIVFAV, (SEQ ID NO: 7)
IVGGGLVLRIVFAV, (SEQ ID NO: 8)
GLRIVFAV,
and
                                (SEQ ID NO: 9)
GLRIVFAVL,
``` wherein each possibility is a separate embodiment of the present invention.

According to another embodiment, the method comprises an isolated peptide comprising the amino acid sequence of general formula I: G-$X_1$-$X_2$-$X_3$-L-$X_4$-I-V-F (SEQ ID NO: 1), wherein $X_1$ is selected from the group consisting of a Leucine and a Glycine amino acid residue; $X_2$ is selected from the group consisting of a Valine and a Leucine amino acid residue; $X_3$ is selected from the group consisting of a Glycine and a Valine amino acid residue; $X_4$ is selected from the group consisting of an Arginine and a Glutamic acid amino acid residue; or an analog or derivative thereof.

According to particular embodiments, the method comprises an isolated peptide comprising the amino acid sequence of general formula I, wherein $X_1$ is a Leucine, $X_2$ is a Valine and $X_3$ is a Glycine residue. According to some embodiments, the method comprises a peptide selected from the group consisting of: SEQ ID NO: 2-SEQ ID NO: 6. Each possibility is a separate embodiment of the present invention.

According to another embodiment, the method comprises a peptide comprising the amino acid sequence GLVGLRIVF (SEQ ID NO: 6). According to an exemplary embodiment, the method comprises a peptide consisting of the amino acid sequence GLVGLRIVF (SEQ ID NO: 6).

According to another embodiment, the method comprises a peptide wherein $X_1$ is a Glycine, $X_2$ is a Leucine, $X_3$ is a Valine and $X_4$ is an Arginine residue. ording to another embodiment, the method comprises a peptide consisting SEQ ID NO: 7.

According to another embodiment, the method comprises a peptide further comprising 1-3 basic amino acid residues contiguous to at least one of the peptide's termini. According to particular embodiments, the basic amino acid residue is independently selected from Lysine and Arginine residues. In one embodiment, the 1-4 basic amino acid residues are contiguous to the N-terminus of said peptide. In another embodiment, said 1-4 basic amino acid residues are contiguous to the C-terminus of said peptide. In an additional embodiment, said 1-4 basic amino acid residues are contiguous to the C-terminus and N-terminus of said peptide. According to one particular embodiment, the method comprises an isolated peptide consisting of the amino acid sequence KKKLFIMIVGGLVGLRIVFAVLSIVKKK (SEQ ID NO: 10).

According to another embodiment, the method comprises a peptide comprising at least one, at least two, at least three D amino acids. According to another embodiment, the D amino acid is selected from Valine, Leucine, Arginine, Glutamic acid, Alanine and Phenylalanine, wherein each possibility is a separate embodiment of the present invention.

According to some embodiments, the method comprises an isolated peptide selected from the group consisting of:

```
                                (SEQ ID NO: 11)
LFIMIvGGLVGlRIVFAVLSIV, (SEQ ID NO: 12)
IvGGLvGLrIVFAvL, (SEQ ID NO: 13)
IVGGGlVLRIVfAV, (SEQ ID NO: 14)
IVGGGLVLrIVFAV, (SEQ ID NO: 15)
IVGGGLvLRIvFAV, (SEQ ID NO: 16)
IVGGlVGLeIVFaV, (SEQ ID NO: 17)
GlVGLrIVF, (SEQ ID NO: 18)
GlvGLrIvF, (SEQ ID NO: 19)
GLrIVFAV, (SEQ ID NO: 20)
GLRIVfAV,
and
                                (SEQ ID NO: 21)
GlRIVFaVL,
``` wherein "v" denotes D-Val, "l" denotes D-Leu, "r" denotes D-Arg, "e" denotes D-Glu, "a" denotes D-Ala, and "f" denotes D-Phe, wherein each possibility is a separate embodiment of the present invention.

According to another embodiment, the method comprises an isolated peptide conjugated to a hydrophobic moiety. According to another embodiment, the hydrophobic moiety is conjugated to the N-terminus or C-terminus of said isolated peptide. According to another embodiment, the hydrophobic moiety is selected from the group consisting of a fatty acid, a sterol and a vitamin.

According to another embodiment, the fatty acid is selected from the group consisting of: octanoic acid, decanoic acid, undecanoic acid, dodecanoic acid, myristic acid, palmitic acid, stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, and cerebronic acid. According to another embodiment, the fatty acid is selected from the group consisting of: undecanoic acid, octanoic acid and myristic acid.

According to another embodiment, said isolated peptide conjugated to a hydrophobic moiety is selected from the group consisting of:

```
                                        (SEQ ID NO: 22)
Undecanoic acid-IVGGGLVLRIVFAV, (SEQ ID NO: 23)
IVGGGLvLRIvFAv-Undecanoic acid, (SEQ ID NO: 24)
Cholesterol-IVGGGLvLRIvFAv, (SEQ ID NO: 25)
IVGGGLvLRIvFAv-Cholesterol, (SEQ ID NO: 26)
Vitamin E-IVGGGLvLRIvFAv, (SEQ ID NO: 27)
Octanoic acid-IVGGlVGLeIVFaV, (SEQ ID NO: 28)
Octanoic acid-GlVGLrIVF, (SEQ ID NO: 29)
Vitamin E-GlvGLrIvF, (SEQ ID NO: 30)
Cholesterol-GLrIVFAV, (SEQ ID NO: 31)
GLRIVfAV-Cholesterol, (SEQ ID NO: 32)
GLRIVFAV-Cholesterol,
and (SEQ ID NO: 33)
GLRIVfAV-Myristic acid,
``` wherein "v" denotes D-Val, "l" denotes D-Leu, "r" denotes D-Arg, "e" denotes D-Glu, "a" denotes D-Ala, and "f" denotes D-Phe, wherein each possibility is a separate embodiment of the present invention.

An inflammatory disease or disorder, according to certain embodiments of the invention, is a disease or disorder associated with T cell activation (e.g., a T cell mediated disease or disorder). An inflammatory disease or disorder according to another embodiment of the invention is a disease or disorder associated with macrophage activation. According to another embodiment, the inflammatory disease or disorder is associated with excessive TNF-α secretion (e.g., from activated macrophages).

According to certain embodiments of the invention, an inflammatory disease or disorder is an autoimmune disease. According to certain embodiments, the autoimmune disease is selected from the group consisting of: multiple sclerosis (MS), autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis), autoimmune hepatitis, rheumatoid arthritis, idiopathic thrombocytopenia, scleroderma, alopecia greata, glomerulonephritis, dermatitis and pemphigus, wherein each possibility represents a separate embodiment of the present invention. According to a particular embodiment, the autoimmune disease is multiple sclerosis.

According to another embodiment, the inflammatory disease or disorder is a TNF-α associated pathology. According to another embodiment, the inflammatory disease or disorder is selected from the group consisting of: asthma, chronic obstructive pulmonary disease (COPD), allergic rhinitis, allergic conjunctivitis, respiratory distress syndrome, chronic bronchitis, nephritis, rheumatoid spondylitis, osteoarthritis, atopic dermatitis, eosinophilic granuloma, psoriasis, sepsis, rheumatoid septic shock, ulcerative colitis, multiple sclerosis, chronic inflammation, Crohn's syndrome and central nervous system (CNS) disorder, wherein each possibility represents a separate embodiment of the present invention. According to a particular embodiment, the inflammatory disease or disorder is asthma. According to yet another particular embodiment, the inflammatory disease or disorder is sepsis.

According to particular embodiments, the inflammatory disease or disorder is selected from the group consisting of: allograft rejection and graft-versus-host disease, wherein each possibility represents a separate embodiment of the present invention.

According to another aspect, the present invention provides a method of inhibiting T-cell activation and/or monocoyte (or macrophage) activation in a subject in need thereof, comprising administering to the subject a therapeutically effective amount of a pharmaceutical composition comprising an isolated peptide of 5-30 amino acids derived from the amino acid sequence LFIMIVGGLVGLRIVFAVLSIV (SEQ ID NO: 2), or an analog or derivative thereof.

According to another aspect, the present invention provides an isolated peptide of 5-30 amino acids derived from the amino acid sequence LFIMIVGGLVGLRIVFAVLSIV (SEQ ID NO: 2), or an analog or derivative thereof, or a pharmaceutical composition comprising same, for use in treating an inflammatory disease or disorder. According to another embodiment, the present invention provides an isolated peptide of 5-30 amino acids derived from the amino acid sequence LFIMIVGGLVGLRIVFAVLSIV (SEQ ID NO: 2), or an analog or derivative thereof, or a pharmaceutical composition comprising same, for use in treating a T-cell and/or monocoyte associated disease or disorder.

According to yet another aspect, the present invention provides use of the peptides of the invention, or the pharmaceutical compositions comprising same, in the preparation of a medicament for treating an inflammatory disease or disorder. According to another embodiment, the present invention provides use of the peptides of the invention, or the pharmaceutical compositions comprising same, in the preparation of a medicament for treating a T-cell and/or monocoyte associated disease or disorder.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
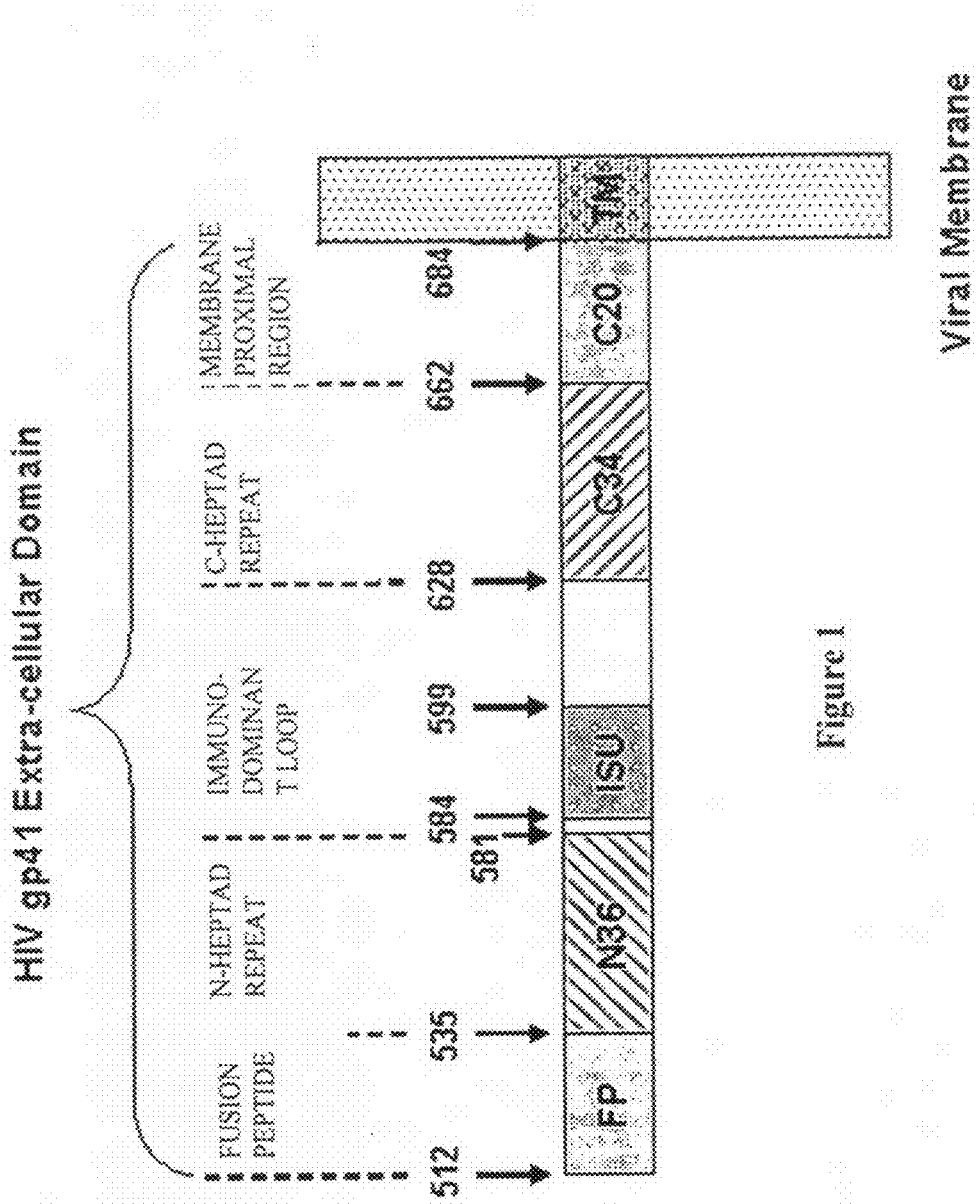
FIG. 1 depicts the functional domains of HIV-1 gp41 extracellular domain.

The present invention provides peptides, derivatives, analogs and lipopeptides comprising an amino acid sequence derived from the HIV gp41 transmembrane domain and to pharmaceutical compositions comprising same effective in preventing or treating T cell mediated diseases and disorders, including but not limited to inflammatory diseases, autoimmunity and graft rejection. The peptides and pharmaceutical compositions of the present invention are useful in treating pathologies associated with monocyte activation, and particularly with TNF-α signaling.

As exemplified herein below, the gp41 transmembrane domain as set forth in SEQ ID NO: 2, co-localized with the CD3/TCR complex in the T cell membrane and interfered with antigen-triggered T cell activation. Remarkably, a fragment of the gp41 transmembrane domain (SEQ ID NO: 6; also designated herein as gp41$_{11\text{-}19}$) showed a stronger immunosuppressive activity than did the full length transmembrane domain. It is noteworthy that the peptides of the present invention exhibited immunosuppressive activity against T-cells activated by myelin oligodendrocyte glycoprotein (MOG) 35-55, a peptide known to play a role in autoimmune diseases, particularly multiple sclerosis.

It if further disclosed that the TMD of gp41 interferes with the immune response mediated by TLR2 and TLR4 towards their respective ligands, LTA and LPS. Surprisingly, the gp41 TMD peptides inhibit TNFα secretion from RAW264.7 macrophage cells.

Thus, the present invention provides anti-inflammatory peptides useful in treating T cell and/or monocyte mediated diseases or disorders.

According to one aspect, the present invention provides an isolated peptide of 9-30 amino acids or a fragment of at least 5 amino acids, an analog or derivative thereof, the peptide comprises the amino acid sequence of general formula I:

G-X$_1$-X$_2$-X$_3$-L-X$_4$-I-V-F (SEQ ID NO: 1)    I wherein X$_1$ is selected from the group consisting of a Leucine and a Glycine amino acid residue; X$_2$ is selected from the group consisting of a Valine and a Leucine amino acid residue; X$_3$ is selected from the group consisting of a Glycine and a Valine amino acid residue; X$_4$ is selected from the group consisting of an Arginine and a Glutamic acid amino acid residue.

According to another embodiment, the isolated peptide comprises the sequence of general formula I, wherein X$_1$ is a Leucine, X$_2$ is a Valine and X$_3$ is a Glycine residue. According to yet another embodiment, the sequence of general formula I, wherein X$_1$ is a Leucine, X$_2$ is a Valine, X$_3$ is a Glycine and X$_4$ is an Arginine residue. According to certain embodiments, the isolated peptide of general formula I has an amino acid sequence selected from the group consisting of: SEQ ID NO: 2-SEQ ID NO: 4 and SEQ ID NO: 6.

According to yet another embodiment, the sequence of general formula I, wherein X$_1$ is a Leucine, X$_2$ is a Valine, X$_3$ is a Glycine and X$_4$ is a Glutamic acid residue. According to a certain embodiment, the isolated peptide of general formula I has an amino acid sequence of SEQ ID NO: 5.

According to an additional embodiment, the isolated peptide consists of the SEQ ID NO: 1 or an analog of at least 70%, at least 75%, at least 80%, at least 85%, at least 90% or at least 95% sequence identity to SEQ ID NO:1, wherein each possibility represent a separate embodiment of the invention.

According to another embodiment the present invention provides an isolated peptide of 5-30 amino acids, or an analog, derivative or a salt thereof, comprising a sequence of 5-20 amino acids derived from SEQ ID NO: 2, wherein the sequence of 5-20 amino acids comprises a sequence having at least 70% at least 75%, at least 80%, at least 85%, at least 90% or at least 95% sequence identity to the sequence GLVGL-RIVF (SEQ ID NO: 6)), wherein each possibility represents a separate embodiment of the present invention.

According to another embodiment, the sequence of 5-20 amino acids consists of 5-15 amino acids, 5-12 amino acids, 9-12 amino acids or 8-10 amino acids, wherein each possibility represents a separate embodiment of the present invention.

Percentage sequence identity can be determined, for example, by the Fitch et al. version of the algorithm (Fitch et al, Proc. Natl. Acad. Sci. U.S.A. 80: 1382-1386 (1983)) described by Needleman et al, (Needleman et al, J. Mol. Biol. 48: 443-453 (1970)), after aligning the sequences to provide for maximum homology. Alternatively, the determination of percent identity between two sequences can be accomplished using the mathematical algorithm of Karlin and Altschul (1993) Proc. Natl. Acad. Sci. USA 90:5873-5877. Such an algorithm is incorporated into the BLASTP program of Altschul et al. (1990) J. Mol. Biol. 215, 403-410. BLAST protein searches are performed with the BLASTP program to obtain amino acid sequences homologous to SEQ ID NO: 4. To obtain gapped alignments for comparative purposes, Gapped BLAST is utilized as described in Altschul et al (1997)

Nucleic Acids Res. 25:3389-3402. When utilizing BLAST and Gapped BLAST programs, the default parameters of the respective programs (e.g., XBLAST) are used.

The present invention further provides fragments, analogs and chemical modifications of the peptides of the present invention as long as they are useful as anti-inflammatory and/or anti-cancer agent (e.g., capable of modulating T cell and/or monocyte activity). It should be understood that the fragments, analogs and chemical modifications of the peptides according to the principles of the present invention do not include any known peptide thereof.

The term "peptide" as used herein encompasses native peptides (degradation products, synthetic peptides or recombinant peptides), peptidomimetics (typically including non peptide bonds or other synthetic modifications) and the peptide analogues peptoids and semipeptoids, and may have, for example, modifications rendering the peptides more stable while in the body or more capable of penetrating into cells. Peptides typically consist of a sequence of about 3 to about 50 amino acids. According to a particular embodiment, the isolated peptides of the present invention consist of 5-50 amino acids, 5-45 amino acids, 5-40 amino acids, 5-35 amino acids, 6-30 amino acids, 5-28 amino acids, 5-26 amino acids, 5-24 amino acids, 5-22 amino acids, 5-20 amino acids, 6-18 amino acids, 5-16 amino acids, 5-14 amino acids, 5-12 amino acids or 5-10 amino acids, wherein each possibility represents a separate embodiment of the present invention.

According to another embodiment, the peptides of the present invention consists of at least 5 amino acids, at least 6 amino acids, at least 7 amino acids, at least 8 amino acids or at least 9 amino acids, wherein each possibility represents a separate embodiment of the present invention.

According to yet another embodiment, the peptides of the present invention consists of at most 50, at most 45, at most 40, at most 35, at most 30, at most 28 amino acids, at most 26 amino acids, at most 24 amino acids, at most 22 amino acids, at most 20 amino acids, at most 18 amino acids, at most 16 amino acids, at most 14 amino acids, at most 12 amino acids or at most 10 amino acids, wherein each possibility represents a separate embodiment of the present invention.

According to particular embodiments, the present invention provides a peptide of 5-30 amino acids derived from the amino acid sequence LFIMIVGGLVGLRIVFAVLSIV (SEQ ID NO: 2), or an analog or derivative thereof, comprising at least one modification selected from the group consisting of:
  (i) 1-3 basic amino acid residues contiguous to at least one of said peptide's termini;
  (ii) said peptide comprising at least one D amino acid; and
  (iii) conjugation of said peptide to a hydrophobic moiety.

According to some embodiments, the peptide comprising at least one D amino acid is an amino acid sequence selected from SEQ ID NO: 2-SEQ ID NO: 10. According to some embodiments, the isolated peptide conjugated to a hydrophobic moiety (e.g., the lipophilic conjugates of the invention) is selected from the group consisting of SEQ ID NO:22 to SEQ ID NO:33.

The terms "polypeptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "isolated peptide" refers to a peptide that is essentially free from contaminating cellular components, such as carbohydrate, lipid, or other proteinaceous impurities associated with the peptide in nature. Typically, a preparation of isolated peptide contains the peptide in a highly purified form, i.e., at least about 80% pure, at least about 90% pure, at least about 95% pure, greater than 95% pure, or greater than 99% pure.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D). Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W) (see, e.g., Creighton, Proteins, 1984).

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

The phrase "conservative substitution" also includes the use of a chemically derivatized residue in place of a non-derivatized residue provided that such peptide displays the requisite function of as specified herein.

The term "derived from" or "corresponding to" refers to construction of a peptide based on the knowledge of a sequence using any one of the suitable means known to one skilled in the art, e.g. chemical synthesis in accordance with standard protocols in the art. A peptide derived from, or corresponding to HIV gp41 transmembrane domain can be an analog, fragment, conjugate (e.g. a lipopeptide conjugate) or derivative of a native gp41 transmembrane sequence, and salts thereof, as long as said peptide retains its ability to inhibit T cell and/or monocyte activation, or inhibit TNF-α signaling.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-$NH_2$ acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —$CH_2$—NH—, —$CH_2$—S—, —$CH_2$—S═O, O═C—NH—, —$CH_2$—O—, —$CH_2$—$CH_2$—, S═C—NH—, and —CH═CH—, and backbone modifications such as modified peptide bonds. Peptide bonds (—CO—NH—) within the peptide can be substituted, for example, by N-methylated bonds (—N(CH3)—CO—); ester bonds (—C(R)H—C—O—O—C(R)H—N); ketomethylene bonds (—CO—CH2—); α-aza bonds (—NH—N(R)—CO—), wherein R is any alkyl group, e.g., methyl; carba bonds (—CH2—NH—); hydroxyethylene bonds (—CH(OH)—CH2—); thioamide bonds (—CS—NH); olefinic double bonds (—CH═CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (MeAla), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The present invention further includes chemical derivatives of the hydrophobic moieties (e.g., fatty acid) conjugated to the peptides of the invention.

The invention further includes peptide analogs, which can contain one or more D-isomer forms of the amino acids. Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein.

According to a particular embodiment, the peptides of the present invention are diastereomeric peptides. The diastereomeric peptides are highly advantageous over all L- or all D-amino acid peptides having the same amino acid sequence because of their higher water solubility, lower immunogenicity (see, for example, Benkirane, N., et al., 1993, J. Biol. Chem. 268: 26279-26285), and lower susceptibility to proteolytic degradation. Such characteristics endow the diastereomeric peptides with higher efficacy and higher bioavailability than those of the all L or all D-amino acid peptides comprising the same amino acid sequence.

The term "diastereomeric peptide" as used herein refers to a peptide comprising both L-amino acid residues and D-amino acid residues. The number and position of D-amino acid residues in a diastereomeric peptide of the preset invention may be variable so long as the peptides are capable on modulating the immune system's innate response. In some embodiments, the peptides comprises at least 2 D-amino acid residues, at least 3 D-amino acid residues, at least 4 D-amino acid residues, at least 5 D-amino acid residues, at least 6 D-amino acid residues, at least 7 D-amino acid residues, at least 8 D-amino acid residues, at least 9 D-amino acid residues, wherein each possibility represents a separate embodiment of the invention.

According to some embodiments, the diastereomeric peptide of the present invention is selected from the group consisting of SEQ ID NO: 11-SEQ ID NO: 21.

The peptides of the invention may be synthesized or prepared by techniques well known in the art. The peptides can be synthesized by a solid phase peptide synthesis method of Merrifield (see J. Am. Chem. Soc., 85:2149, 1964). Alternatively, the peptides of the present invention can be synthesized using standard solution methods well known in the art (see, for example, Bodanszky, M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group, suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5-dimethoxybenzyloxycarbonyl, o-nitrophenylsulfenyl, 2-cyano-t-butyloxycarbonyl, 9-fluorenylmethyloxycarbonyl (FMOC) and the like. The BOC or FMOC protecting group is preferred.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

The peptides of the present invention, analogs, or derivatives thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

Included within the scope of the invention are peptide conjugates comprising the peptides of the present invention derivatives, or analogs thereof joined at their amino or carboxy-terminus or at one of the side chains via a peptide bond to an amino acid sequence of a different protein. Conjugates comprising peptides of the invention and a protein can be made by protein synthesis, e.g., by use of a peptide synthesizer, or by ligating the appropriate nucleic acid sequences encoding the desired amino acid sequences to each other by methods known in the art, in the proper coding frame, and expressing the conjugate by methods commonly known in the art. Additionally or alternatively, the peptides of the present invention, derivatives, or analogs thereof can be joined to another moiety such as, for example, a fatty acid, a sugar moiety, arginine residues, hydrophobic moieties, and any known moiety that facilitate membrane or cell penetration.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

Hydrophobic Moieties

According to a particular embodiment, there is provided a lipopeptide, wherein the peptide of the invention is coupled (or conjugated) to a hydrophobic moiety. The lipopetide inhibit T cell activation or proliferation and/or monocyte activation, thereby useful as anti-inflammatory agents and/or anti-cancer agents. The terms "lipopeptide" and "lipophilic conjugate" as used herein refer to a peptide covalently coupled to a hydrophobic moiety.

The term "hydrophobic" refers to the tendency of chemical moieties with nonpolar atoms to interact with each other rather than water or other polar atoms. Materials that are "hydrophobic" are, for the most part, insoluble in water. Non limiting examples of natural products with hydrophobic properties include lipids, fatty acids, phospholipids, sphingolipids, acylglycerols, waxes, sterols, steroids, terpenes, prostaglandins, thromboxanes, leukotrienes, isoprenoids, retinoids, biotin, and hydrophobic amino acids such as tryptophan, phenylalanine, isoleucine, leucine, valine, methionine, alanine, proline, and tyrosine. A chemical moiety is also hydrophobic or has hydrophobic properties if its physical properties are determined by the presence of nonpolar atoms. The term includes lipophilic groups.

The term "lipophilic group", in the context of being attached to a peptide, refers to a group having high hydrocarbon content thereby giving the group high affinity to lipid phases. A lipophilic group can be, for example, a relatively long chain alkyl or cycloalkyl (preferably n-alkyl) group having approximately 6 to 30 carbons. The alkyl group may terminate with a hydroxyl, primary amine or any other reactive group. To further illustrate, lipophilic molecules include naturally-occurring and synthetic aromatic and non-aromatic moieties such as fatty acids, esters and alcohols, other lipid molecules, cage structures such as adamantane, and aromatic hydrocarbons such as benzene, perylene, phenanthrene, anthracene, naphthalene, pyrene, chrysene, and naphthacene.

According to some embodiments of the present invention, the hydrophobic moiety may be coupled to the N-terminal, to the C-terminal, or to any other free functional group along the peptide chain, wherein each possibility represents a separate embodiment of the present invention. For example the conjugation of a palmitic acid or other fatty acids, Vitamin E, cholesterol and sphingosine to the N or C terminus of the peptide. According to particular embodiments, said isolated peptide conjugated to a hydrophobic moiety is selected from the group consisting of SEQ ID NO: 22-SEQ ID NO:33.

The terms "coupling" and "conjugation" are used herein interchangeably and refer to the chemical reaction, which results in covalent attachment of a hydrophobic moiety to a peptide to yield a lipophilic conjugate. Coupling of a hydrophobic moiety to a peptide is performed similarly to the coupling of an amino acid to a peptide during peptide synthesis. Alternatively, the coupling of a hydrophobic moiety to a peptide may be performed by any coupling method known in the art. It should be understood that the hydrophobic moiety is covalently coupled to the peptide.

According to some embodiments, the hydrophobic moiety comprises an aliphatic group and a reactive group through which the aliphatic group may be linked to the peptide. Non limiting examples of such reactive groups include: a carboxyl group, a carbonyl group, an amine group, a thiol group, a hydroxyl group, a maleimide, an imido ester, an N-hydroxysuccinimide, alkyl halide, and aryl azide.

The term "aliphatic", "aliphatic group" or "aliphatic chain, as used herein, means a straight-chain (i.e., unbranched) or branched, substituted or unsubstituted hydrocarbon chain that is completely saturated or that contains one or more unsaturated bonds. Unless otherwise specified, aliphatic groups contain at least aliphatic carbon atoms. In some embodiments, aliphatic groups contain between 6 and 30 aliphatic carbon atoms. In other embodiments, aliphatic groups contain at least 8 aliphatic carbon atoms. In other embodiments, aliphatic groups contain at least 10 aliphatic carbon atoms. In still other embodiments, aliphatic groups contain at least 12 aliphatic carbon atoms, and in yet other embodiments aliphatic groups contain at least 16 aliphatic carbon atoms. Suitable aliphatic groups include, but are not limited to, linear or branched, substituted or unsubstituted alkyl, alkenyl, alkynyl, and heteroalkyl groups.

The term "alkyl" refers to a saturated, linear or branched hydrocarbon moiety, such as —$CH_3$—$(CH_2)_4$—$CH_2$; —$CH_2$—$(CH_2)_5$—$CH_2$, $CH_3$—$(CH_2)_6$—$CH_2$, $CH_3$—$(CH_2)_7$—$CH_2$, $CH_3$—$(CH_2)_8$—$CH_2$, $CH_3$—$(CH_2)_9$—$CH_2$, $CH_3$—$(CH_2)_{10}$—$CH_2$, $CH_3$—$(CH_2)_{11}$—$CH_2$, $CH_3$—$(CH_2)_{12}$—$CH_2$; $CH_3$—$(CH_2)_{13}$—$CH_2$, $CH_3$—$(CH_2)_{14}$—$CH_2$.

The term "alkenyl" as used herein, denotes a divalent group derived from a straight chain or branch hydrocarbon moiety having at least one carbon-carbon double bond.

The term "heteroalkyl" refers to an alkyl or an alkenyl moiety having at least one heteroatom (e.g., N, O, or S). Preferred are heteroalkylenes having at least one O.

The term "unsaturated", as used herein, means that a moiety has one or more units of unsaturation.

According to some currently preferred embodiments, the hydrophobic moiety is a fatty acid.

Fatty Acids:

The fatty acid that can be coupled to the peptides of the invention is selected from saturated, unsaturated, monounsaturated, and polyunsaturated fatty acids, wherein each possibility is a separate embodiment of the present invention. Typically, the fatty acid consists of at least four, carbon atoms, at least six carbon atoms, preferably, at least eight carbon atoms. According to some embodiments, the fatty acid is an essential fatty acid. "Essential fatty acids" may refer to certain fatty acids, in particular polyunsaturated fatty acids that an organism must ingest in order to survive, being unable to synthesize the particular essential fatty acid de novo. Examples include the essential fatty acid C9, C12-linoleic acid and their structural variants. Essential fatty acids may be found in nature or produced synthetically. Non limiting examples to fatty acids according to some embodiments of the invention include: butyric acid, decanoic acid (DA), undecanoic acid (UA), dodecanoic acid (lauric acid), myristic acid (MA), palmitic acid (PA), stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, docosahexaenoic acid (DHA), eicosapentaenoic acid, stearidonic acid, eicosatrienoic acid, eicosatetraenoic acid, docosapentaenoic acid and cerebronic acid. conjugated linolenic acid, omega 3 fatty acids (for example: docosahexaenoic acid (DHA), eicosapentaenoic acid, α-linolenic acid, stearidonic acid eicosatrienoic acid, eicosatetraenoic acid, docosapentaenoic acid and glycerol ester derivatives thereof), omega 6 fatty acids (for example: linoleic acid, gamma-linolenic acid, eicosadienoic acid, dihomo-gamma-linolenic acid, arachidonic acid, docosadienoic acid, adrenic acid, docosapentaenoic acid and calendic acid), omega 9 fatty acids (for example: oleic acid, eicosenoic acid, mead acid, erucic acid and nervonic acid), polyunsaturated fatty acids, long-chained polyunsaturated fatty acids, arachidonic acid, monounsaturated fatty acids, precursors of fatty acids, and derivatives of fatty acids, wherein each possibility is a separate embodiment of the present invention.

It should be emphasized that any fatty acid could be coupled to the peptides of the invention so long as the anti-inflammatory or immunosuppressive activity (e.g., inhibition of T cell activation and/or proliferation) or anti-cancer activity (e.g., reduced TNF-α signaling) of the conjugate is enhanced.

Vitamins:

In certain embodiments, the present invention relates to vitamins selected from the group consisting of: vitamin A, vitamin D, vitamin E and vitamin K, wherein each possibility is a separate embodiment of the present invention. According to other embodiments, the present invention relates to any other vitamin, salts and derivatives thereof known in the art. According to other embodiments, the vitamins can be from any source known in the art. According to certain embodiments the vitamin D is selected from the group consisting of vitamin D2 (ergocalciferol), vitamin D3 (cholecalciferol) and any other vitamin D or its derivatives known in the art. According to other embodiments, the present invention relates to vitamin D salts and derivatives thereof. According to other embodiments, the vitamin E is selected from the group consisting of α, β, γ, δ-tocopherols and α, β, γ, or δ-tocotrienol and any other vitamin E known in the art. According to other embodiments, the present invention relates to vitamin E salts (e.g., vitamin E phosphate) and derivatives (e.g., tocopheryl sorbate, tocopheryl acetate, tocopheryl succinate, and other tocopheryl esters). According to additional embodiments, the vitamin A is selected from the group consisting of retinol, retinal, retinoic acid and any other vitamin A known in the art. According to other embodiments, the present invention relates to vitamin A salts and derivatives thereof. According to other embodiments, the vitamin K is selected from the group consisting of vitamin K1 (phytonadione), vitamin K2 (menaquinone), vitamin K3 (menadione), vitamin K4, vitamin K5, vitamin K6, vitamin K7, and their salts and derivatives.

Sterols:

According to one embodiment refers to a steroid with a hydroxyl group at the 3-position of the A-ring. In another embodiment, the sterol is a zoosterol. According to one embodiment, the zoosterol is cholesterol or derivatives thereof. In yet another embodiment, the sterol is a phytosterols. Non limiting examples of phytosterols include stigmasterol, beta-sitosterol, campesterol, ergosterol (provitamin D2), brassicasterol, delta-7-stigmasterol and delta-7-avenasterol, wherein each possibility is a separate embodiment of the present invention.

Polynucleotide

According to another aspect, the present invention provides an isolated polynucleotide sequence encoding the peptides of the present invention (i.e., a peptide derived from SEQ ID NO:2, the gp41 transmembrane domain), or an analog or a conjugate thereof.

The term "polynucleotide" means a polymer of deoxyribonucleic acid (DNA), ribonucleic acid (RNA) or a combination thereof, which can be derived from any source, can be single- or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a peptide or protein if transcription and translation of mRNA corresponding to that gene produces the peptide or protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the peptide or protein or other product of that gene or cDNA.

One who is skilled in the art will appreciate that more than one polynucleotide may encode any given peptide or protein in view of the degeneracy of the genetic code and the allowance of exceptions to classical base pairing in the third position of the codon, as given by the so-called "Wobble rules." It is intended that the present invention encompass polynucleotides that encode the peptides of the present invention as well as any analog thereof.

A polynucleotide of the present invention can be expressed as a secreted peptide where the peptides of the present invention or analog thereof is isolated from the medium in which the host cell containing the polynucleotide is grown, or the polynucleotide can be expressed as an intracellular peptide by deleting the leader or other peptides, in which case the peptides of the present invention or analog thereof is isolated from the host cells. The peptides of the present invention or analog thereof are then purified by standard protein purification methods known in the art.

The peptides of the present invention, analogs, or derivatives thereof can also be provided to the tissue of interest by transferring an expression vector comprising an isolated polynucleotide encoding the peptides of the present invention, or analog thereof to cells associated with the tissue of interest. The cells produce the peptide such that it is suitably provided to the cells within the tissue to exert a biological activity such as, for example, to reduce or inhibit inflammatory processes within the tissue of interest.

The expression vector according to the principles of the present invention further comprises a promoter. In the context of the present invention, the promoter must be able to drive the expression of the peptide within the cells. Many viral promoters are appropriate for use in such an expression vector (e.g., retroviral ITRs, LTRs, immediate early viral promoters (IEp) (such as herpes virus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the peptides of the present invention, or analog thereof and the promoter are operably linked such that the promoter is able to drive the expression of the polynucleotide. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors are introduced into the cells in a manner such that they are capable of expressing the isolated polynucleotide encoding the peptides of the present invention or analog thereof contained therein. Any suitable vector can be so employed, many of which are known in the art. Examples of such vectors include naked DNA vectors (such as oligonucleotides or plasmids), viral vectors such as adeno-associated viral vectors (Berns et al., 1995, Ann. N.Y. Acad. Sci. 772:95-104, the contents of which are hereby incorporated by reference in their entirety), adenoviral vectors, herpes virus vectors (Fink et al., 1996, Ann. Rev. Neurosci. 19:265-287), packaged amplicons (Federoff et al., 1992, Proc. Natl. Acad. Sci. USA 89:1636-1640, the contents of which are hereby incorporated by reference in their entirety), papilloma virus vectors, picornavirus vectors, polyoma virus vectors, retroviral vectors, SV40 viral vectors, vaccinia virus vectors, and other vectors. Additionally, the vector can also include other genetic elements, such as, for example, genes encoding a selectable marker (e.g., β-gal or a marker conferring resistance to a toxin), a pharmacologically active protein, a transcription factor, or other biologically active substance.

Methods for manipulating a vector comprising an isolated polynucleotide are well known in the art (e.g., Sambrook et al., 1989, Molecular Cloning: A Laboratory Manual, 2d edition, Cold Spring Harbor Press, the contents of which are hereby incorporated by reference in their entirety) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising the polynucleotide of interest is introduced into the cells by any means appropriate for the transfer of DNA into cells. Many such methods are well known in the art (e.g., Sambrook et al., supra; see also Watson et al., 1992, Recombinant DNA, Chapter 12, 2d edition, Scientific American Books, the contents of which are hereby incorporated by reference in their entirety). Thus, in the case of prokaryotic cells, vector introduction can be accomplished, for example, by electroporation, transformation, transduction, conjugation, or mobilization. For eukaryotic cells, vectors can be introduced through the use of, for example, electroporation, transfection, infection, DNA coated microprojectiles, or protoplast fusion. Examples of eukaryotic cells into which the expression vector can be introduced include, but are not limited to, ovum, stem cells, blastocytes, and the like.

Cells, into which the polynucleotide has been transferred under the control of an inducible promoter if necessary, can be used as transient transformants. Such cells themselves may then be transferred into a subject for therapeutic benefit therein. Thus, the cells can be transferred to a site in the subject such that the peptide of the invention is expressed therein and secreted therefrom and thus reduces or inhibits, for example, cancerous processes so that the clinical condition of the subject is improved. Alternatively, particularly in the case of cells to which the vector has been added in vitro, the cells can first be subjected to several rounds of clonal selection (facilitated usually by the use of a selectable marker sequence in the vector) to select for stable transformants. Such stable transformants are then transferred to a subject, preferably a human, for therapeutic benefit therein.

Within the cells, the polynucleotide encoding the peptides of the present invention, or analog thereof is expressed, and optionally is secreted. Successful expression of the polynucleotide can be assessed using standard molecular biology techniques (e.g., Northern hybridization, Western blotting, immunoprecipitation, enzyme immunoassay, etc.).

The present invention encompasses transgenic animals comprising an isolated polynucleotide encoding the peptides of the invention.

Pharmaceutical Compositions

The present invention provides a pharmaceutical composition comprising a pharmaceutically acceptable carrier and as an active ingredient an isolated peptide of 9-30 amino acids comprising the amino acid sequence of G-$X_1$-$X_2$-$X_3$-L-$X_4$-I-V-F (SEQ ID NO: 1), wherein $X_1$ is selected from the group consisting of a Leucine and a Glycine amino acid residue; $X_2$ is selected from the group consisting of a Valine and a Leucine amino acid residue; $X_3$ is selected from the group consisting of a Glycine and a Valine amino acid residue; $X_4$ is selected from the group consisting of an Arginine and a Glutamic acid amino acid residue; or an analog or derivative thereof.

According to additional embodiments, the pharmaceutical compositions comprises as an active ingredient a lipopeptide (i.e., the peptide of the invention conjugated to a hydrophobic moiety), and a pharmaceutically acceptable carrier.

The pharmaceutical compositions of the invention can be formulated in the form of a pharmaceutically acceptable salt of the peptides of the present invention or their analogs or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

The term "pharmaceutically acceptable" means suitable for administration to a subject, e.g., a human. For example, the term "pharmaceutically acceptable" can mean approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences by E. W. Martin, the contents of which are hereby incorporated by reference herein. Such compositions will contain a therapeutically effective amount of a gp41 TMD peptide according to the present invention, preferably in a substantially purified form, together with a suitable amount of carrier so as to provide the form for proper administration to the subject.

The amount of the peptides, or lipopeptides, of the present invention, which will be effective in the treatment of a particular disorder or condition will depend on the nature of the disorder or condition and on the particular peptide, or lipopeptide, and can be determined by standard clinical techniques known to a person skilled in the art. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

It will be understood that the pharmaceutical compositions of the present invention can comprise the peptides (or lipopeptides) of the current invention, or a derivative or analog thereof, or all possible combinations of two or more of these peptide derivatives, or analogs or other sources of the peptide of the current invention. Thus, the pharmaceutical compositions can comprise one or more isolated polynucleotides, one or more expression vectors, or one or more host cells or any combination thereof, according to the principles of the present invention.

Determination of a therapeutically effective amount of a peptide is well within the capability of those skilled in the art, especially in light of the detailed disclosure provided herein.

Toxicity and therapeutic efficacy of the peptides (or lipopetides) described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See, for example, Fingl et al., 1975, in The Pharmacological Basis of Therapeutics, Ch. 1 p. 1, the contents of which are hereby incorporated by reference in their entirety).

Depending on the severity and responsiveness of the condition to be treated, dosing can also be a single administration of a slow release composition, with course of treatment lasting from several days to several weeks or until cure is effected or diminution of the disease state is achieved.

It is further understood that the peptides of the invention can be formulated or administered together with additional active ingredients as required to treat the condition of the patient.

Depending on the location of the tissue of interest, the peptides or lipopeptides of the present invention can be supplied in any manner suitable for the provision of the peptide to cells within the tissue of interest. Thus, for example, a composition containing the peptides of the present invention can be introduced, for example, into the systemic circulation, which will distribute the peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

It may be desirable to administer the pharmaceutical composition of the invention locally to the area in need of treatment; this can be achieved by, for example, and not by way of limitation, local infusion, topical application, by injection, by means of a catheter, by means of a suppository, or by means of an implant, said implant being of a porous, non-porous, or gelatinous material. According to some preferred embodiments, administration can be by direct injection e.g., via a syringe, at the site of a damaged tissue.

For topical application, a peptide of the present invention, derivative, or analog thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as a fatty oil. In addition, dosage unit forms can contain various other materials which modify the physical form of the dosage unit, for example, coatings of sugar, shellac, or other enteric agents. The tablets of the invention can further be film coated.

The peptides of the present invention, derivatives or analogs thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

Use of the Peptides

In some aspects, the present invention provides the use of pharmaceutical compositions comprising the peptides derived from the transmembrane domain of HIV gp41 molecule, effective in preventing or treating an inflammatory disease or disorder, such as pathologies associated, or characterized by, T cell and/or monocyte activation.

The term "inflammatory disease" refers to a disease which involves, results at least in part from, or includes inflammation. The term includes, but is not limited to, diseases selected from multiple sclerosis (MS), rheumatoid arthritis (RA), osteoarthritis, ankylosing spondylitis, juvenile idiopathic arthritis, psoriasis, inflammatory bowel diseases, Chrohn's disease, ulcerative colitis, uveitis, inflammatory lung diseases, chronic obstructive pulmonary disease.

T lymphocytes (T cells) are one of a variety of distinct cell types involved in an immune response. The activity of T cells is regulated by antigen, presented to a T cell, by an antigen-presenting cell (APC), in the context of a major histocompatibility complex (MHC) molecule. The T cell receptor (TCR) then binds to the MHC-antigen complex. Once antigen is complexed to MHC, the MHC-antigen complex is bound by a specific TCR on a T cell, thereby altering the activity of that T cell.

Proper activation of T lymphocytes by antigen-presenting cells requires stimulation not only of the TCR, but the combined and coordinated engagement of its co-receptors. Most TCR co-receptors bind cell-surface ligands and are concentrated in areas of cell-cell contact, forming what has been termed an immune synapse. Synapse formation has been associated with the induction of antigen-specific T cell proliferation, cytokine production and lytic granule release, and its function was determined necessary for complete T cell activation (Davis and Dustin, 2004; Huppa et al., 2003).

According to certain aspects, the present invention provides a method for treating pathologies associated, or characterized by, T cell activation. According to some embodiments, the present invention provides a method for treating a T cell mediated disease or disorder. The terms "T cell mediated disease or disorder" and "T-cell mediated pathology" refer to any condition in which an inappropriate or detrimental T cell response is a component of the etiology or pathology of a disease or disorder. The term is intended to include both diseases directly mediated by T cells, and also diseases in which an inappropriate or detrimental T cell response contributes to the production of abnormal antibodies, as well as graft rejection. It should be understood that the term does not include diseases or conditions caused by HIV, such as acquired immune deficiency syndrome (AIDS).

In another embodiment, the invention is directed to the use of an isolated peptide derived from SEQ ID NO: 2, for the preparation of a medicament, for treating or preventing T cell mediated disease and disorders. Typically, the peptide is capable of inhibiting T cell activation.

Monocytes/Macrophages

Monocytes/macrophages play a critical role in managing innate and adaptive immunity-including inflammatory processes by secreting proinflammatory molecules such as TNF-α. The activation of macrophages and monocytes is mediated by activation of various receptors including TLR-4 and their counter molecules such as lipopolysaccharide (LPS) derived from bacteria or virus. In parallel, the activation of these cells triggers various cellular responses such as cell migration, adhesion, extravasation, and infiltration to induce effective movement of these cells into inflamed tissue by adhesion molecules. The molecular interaction between surface receptors and counter molecules seen in various cellular inflammatory responses generates a series of complex signaling events composed of numerous intracellular enzymes such as phosphoinositide-3-kinase (PI3K), phosphoinositide-dependent kinase 1 (PDK1), Akt (protein kinase B), and mitogen-activated protein kinases (MAPKs) such as extracellular signal-regulated kinase (ERK), c-Jun N-terminal kinase (JNK), and p38 linked to actin cytoskeleton rearrangement for modulating cellular activation or the proinflammatory gene expression by mediating with transcription factors like NF-B and AP-1. Recently, inflammatory responses by monocytes and macrophages were reported to be a critical pathological event in triggering various acute or chronic diseases such as septic shock, asthama, autoimmune diseases, cardiovascular diseases, obesity, and diabetes.

According to some aspects, the present invention provides a method for treating a monocyte and/or macrophage mediated disease or disorder. In one embodiment, a monocyte and/or macrophage mediated disease or disorder is asthma. In another embodiment, a monocyte and/or macrophage mediated disease or disorder is sepsis.

In another embodiment, the invention is directed to the use of an isolated peptide derived from SEQ ID NO: 2, for the preparation of a medicament, for treating or preventing a monocyte or macrophage mediated disease and disorders. Typically, the peptide is capable of inhibiting monocyte or macrophage activation and/or inhibiting TNFα secretion from macrophage.

Inflammatory Diseases

In another embodiment, the compositions of the invention are useful for treating a T cell-mediated inflammatory disease. In another embodiment, the compositions of the invention are useful for treating a monocyte or macrophage mediated inflammatory disease. In certain embodiments the compositions are useful in treating an inflammatory disease, including but not limited to: inflammatory or allergic diseases such as asthma, hypersensitivity lung diseases, hypersensitivity pneumonitis, delayed-type hypersensitivity, interstitial lung disease (ILD) (e.g., idiopathic pulmonary fibrosis, or ILD associated with rheumatoid arthritis or other inflammatory diseases); scleroderma; psoriasis (including T-cell mediated psoriasis); dermatitis (including atopic dermatitis and eczematous dermatitis), iritis, conjunctivitis, keratoconjunctivitis, cutaneous lupus erythematosus, scleroderma, vaginitis, proctitis, drug eruptions, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Graves ophthalmopathy and primary biliary cirrhosis. Each possibility represents a separate embodiment of the present invention.

In other embodiments, the composition is useful for treating graft rejection, including allograft rejection or graft-versus-host disease.

Autoimmune Disease

In another embodiment, the compositions of the invention are useful for treating a T cell-mediated autoimmune disease. In another embodiment, the compositions of the invention are useful for treating a monocyte or macrophage mediated autoimmune disease. In one embodiment of the invention, the peptides and compositions are useful for treating an autoimmune disease, including but not limited to: multiple sclerosis (MS), autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis) or autoimmune hepatitis, rheumatoid arthritis. Each possibility represents a separate embodiment of the present invention.

TNFα-Mediated Diseases

In some embodiments the present invention provides peptides, lipopeptides and pharmaceutical composition for the treatment or alleviation of a TNFα mediated disease. In another embodiment, the present invention provides a method of treating a pathology associated with TNF-α in a subject in need thereof, comprising administering to the subject a therapeutically effective amount of a pharmaceutical composition comprising an isolated peptide of 5-30 amino acids derived from the amino acid sequence LFIMIVGGLVGLRIVFAVL-SIV (SEQ ID NO: 2), or an analog or derivative thereof.

TNF has been implicated in both cancer development and progression in some preclinical models (Mocellin and Nitti, 2008). In particular, as a central mediator of inflammation, TNF might represent one of the molecular links between chronic inflammation and the subsequent development of malignant disease. Furthermore, deregulated TNF expression within the tumor microenvironment appears to favor malignant cell tissue invasion, migration and ultimately metastasis formation.

In a particular embodiment, the TNF-α mediated disease (or pathology associated with TNF-α) is cancer. Thus, in some embodiments, the invention provides a method for treatment, alleviation or prevention of tumors or cancer which are mediated by TNF-α. It is contemplated that a tumor, cancerous or precancerous condition wherein the growth and/or proliferation of the tumor or cancerous/precancerous cells are dependent on or facilitated by TNF-α activity or signaling may be sensitive to the peptides of the present invention.

The TNF-α mediated cancer is, in some embodiments, a cancer selected from blood and lymphatic systems, skin cancer, cancer of digestive systems, cancer of urinary systems, breast cancer, ovarian cancer, gynaecological cancer, choriocarcinoma, lung cancer, brain tumor, bone tumor, carcinoid tumor, nasopharyngeal vancer, retroperitoneal sarcoma, soft tissue tumor, thyroid cancer, cancer of unknown primary site, metastase from primary cancers of the skin, breast, colon, prostate, kidney, thyroid, stomach, cervix, rectum, testis, and bone and from melanoma, wherein each possibility is a separate embodiment of the invention.

Methods of treating a disease according to the invention may include administration of the pharmaceutical compositions of the present invention as a single active agent, or in combination with additional methods of treatment. The methods of treatment of the invention may be in parallel to, prior to, or following additional methods of treatment.

The following examples are presented in order to more fully illustrate some embodiments of the invention. They should, in no way be construed, however, as limiting the broad scope of the invention.

EXAMPLES

Peptide Synthesis and Fluorescent Labeling

Peptides were synthesized using the F-moc solid phase method on Rink amide resin (0.68 meq/gm), as previously described (Kliger et al., 1997, *J. Biol. Chem.* 272, 13496-13505). The synthetic peptides were purified (greater than 98% homogeneity) by reverse phase high performance liquid chromatography (RP-HPLC) on a C4 column using a linear gradient of 30-70% acetonitrile in 0.1% trifluoroacetic acid (TFA) for 40 minutes. The peptides were subjected to amino acid and mass spectrometry analysis to confirm their composition. To avoid aggregation of the peptides prior to their use in the cell culture assays, the stock solutions of the concentrated peptides were maintained in dimethyl sulfoxide (DMSO). The final concentration of DMSO in each experiment was lower than 0.25% vol/vol and had no effect on the system under investigation. For NBD-F (4-chloro-7-nitrobenz-2-oxa-1,3-diazole fluoride) fluorescent labeling, resin-bound peptides were treated with NBD-F (2-fold excess) dissolved in dimethyl formamide (DMF), leading to the formation of resin-bound N-terminal NBD peptides (Gerber and Shai, 2000, *J. Biol. Chem.* 275, 23602-23607). After 1 h, the resins were washed thoroughly with DMF and then with methylene chloride, dried under nitrogen flow, and then cleaved for 3 h with TFA 95%, $H_2O$ 2.5%, and triethylsilane 2.5%. For Rho-N fluorescent labeling, the F-moc protecting group was removed from the N-terminus of the resin-bound peptides by incubation with piperidine for 12 min, whereas all the other reactive amine groups of the attached peptides were kept protected. The resin-bound peptides were washed twice with DMF, and then treated with rhodamine-N-hydroxysuccinimide (2-fold excess), in anhydrous DMF containing 2% DIEA, leading to the formation of a resin-bound N-rhodamine peptide. After 24 h, the resin was washed thoroughly with DMF and then with methylene chloride, dried under nitrogen flow, and then cleaved for 3 h with TFA 95%, $H_2O$ 2.5%, and triethylsilane 2.5%. The labeled peptides were purified on a RP-HPLC C4 column as described above. Unless stated otherwise, stock solutions of concentrated peptides were maintained in DMSO to avoid aggregation of the peptides prior to use.

Fluorescence Energy Transfer (FRET)

Preparation of Large Unilamellar Vesicles (LUV)

Thin films of PC were generated after dissolving the lipids in a 2:1 (v/v) mixture of $CHCL_3$/MeOH and drying them under a stream of nitrogen gas while rotating them. The films were lyophilized overnight, sealed with argon gas to prevent oxidation of the lipids, and stored at −20° C. Before the experiments, films were suspended in the appropriate buffer and vortexed for 1.5 min. The lipid suspension underwent five cycles of freezing-thawing and extrusion through polycarbonate membranes with 1- and 0.1-μm diameter pores to create large unilamellar vesicles.

FRET Measurements

The FRET experiments were performed by using NBD and Rho labeled peptides. Fluorescence spectra were obtained at room temperature, with excitation set at 467 nm (10-nm slit) and emission scan at 500-600 nm (10-nm slits). In a typical experiment, a NBD-labeled peptide was added first from a stock solution in DMSO (final concentration 0.1 μM and a maximum of 0.25% (v/v) DMSO) to a dispersion of PC LUV (100 μM) in PBS. This was followed by the addition of Rho labeled peptide in several sequential doses ranging from 0.025 μM to 0.075 μM (stock in DMSO). Fluorescence spectra were obtained before and after addition of the Rho labeled peptide. The fluorescence values were corrected by subtracting the corresponding blank (buffer with the same vesicles concentration). The statistical analysis was performed using ANOVA for the pick measurements at 535 nm (n=3, *p<0.05).

Co-Localization of Peptides with TCR Molecules

Resting MOG35-55 T-cells or after activation for 72 h with MOG35-55 and APC were blocked with 1% BSA at room temperature to block non-specific binding. After 30 min the cells were washed and divided into aliquots containing 100,000 cells per 100 μl, and either gp41 TMD or a control membrane-binding amphipathic peptide (AMP-scr) was added (final concentration of 2 μM) for 1 h at 37° c. The cells were then washed and labeled with the tested antibody for 25 min at RT followed by biotin-conjugated anti-hamster IgG 25 min at RT and Streptavidin PE-Cy-5 10 min at RT (eBioscience San-Diego Calif., USA). Anti-hamster IgG followed by Streptavidin-Cy-5 served as a measure of non-specific binding amphipathic (AMP) peptide served as low TCR affinity control. The cells were analyzed by confocal fluorescence microscopy using Lab-Tek 8 chambers cover-glass (nunc) with living cells. The labeled cell samples were observed under a fluorescence confocal microscope. PE-Cy-5 excitation was done with HeNe laser 633 nm (emission data was collected with filter BA660IF, 660 nm long pass). NBD excitation was done with Ar laser 488 nm (emission data was collected from 505-525 nm). The co-localization percentage was quantified suing the "Simple PCI" software, and calculated as:

(Co-localization fluorescence/NBD fluorescence)×100=co-localization percentage.

T-Cell Activation and Proliferation

T-cells were plated onto round 96-well plates in medium containing RPMI-1640 supplemented with 2.5% fetal calf serum (FCS), 100 U/ml penicillin, 100 μg/ml streptomycin, 50 μM 2β-mercaptoethanol, and 2 mM L-glutamine. $12 \times 10^4$ cells of the T-cell line specific to MOG p35-55, $5 \times 10^5$ irradiated (3000 rad) spleen cells (APC), and 10 μg/ml of MOG p35-55 were added to each well. In addition, peptides corresponding to the gp41 TMD region were added. Each determination was made at least in triplicate.

In order to exclude interaction between the examined peptides and the MOG p35-55 antigen, the MOG p35-55 antigen was initially added to the APCs in a test tube, and in a second test tube, the examined peptides were added to the T-cells. After 1 hour, the APCs and the T-cells were mixed and incubated for 72 h in a 96 well round bottom plate.

For some experiments, T cells were activated with immobilized anti-CD3 antibodies (Kaleeba et al., 1998, *Int. Immunol.* 10, 453-461) or PMA/ionomycin as described (Wang et al., 2002 *Clin. Immunol.* 105, 199-207). After 72 hours, at 37° C. in a 7.5% $CO_2$ humidified atmosphere, the T-cells were pulsed with 1 μCi ($H^3$) thymidine, with a specific activity of 5.0 Ci/mmol, for 7 hours, and ($H^3$) thymidine incorporation was measured using a 96-well plate beta-counter. The mean cpm±Standard Error was calculated for each triplicate or quadruplicate. The results of T-cell proliferation experiments are shown as the percentage of T-cell proliferation inhibition triggered by the antigen in the absence of gp41 TMD peptides.

TNFα Secretion

RAW264.7 macrophage cells were plated in a 96 well plate at a concentration of 20,000 cells per well and grown overnight in RPMI medium supplemented with 10% FBS and 1% Pen-Strep and 1% L-glutamine at 37 degrees with 5% $CO_2$. The following day media was changed and the gp41 TMD peptide was added at a concentration of 20 μM—dissolved in DMSO and diluted 1:100. The cells were incubated in the presence of the peptide for 2 hours afterwards the media was removed and cells were washed twice with 100 μl of fresh media. Lipopolysaccharide (LPS) and Lipoteichoic acid (LTA) ligands were added for 5 hours (LPS was added at the concentration of 10 ng/ml and LTA added at 500 ng/ml; cells were grown at this time with 200 μl). After 5 hours 150 were taken for the measurement of TNFα by an ELISA kit.

Mice

C57BL/6J mice were maintained in a specific pathogen-free facility and were used according to the guidelines and under the supervision of the animal welfare committee.

Bioinformatics Database Analysis

To evaluate the occurrence of TCRα CP-like transmembrane domain (TMD) in viruses, a dataset of putative viral TMDs was constructed based on the viral sub-division within the Uniport Knowledge Base, consisting on the intensively annotated Swiss-Prot database (version 57.10, total of 29,252 entries) (Herrmann et al. J. Mol. Biol. 385: 912-923, 2009). All sequences containing at least one transmembrane annotation in the FT field were extracted from the dataset to create a library of transmembrane viral domains, where every entry is composed from a distinct putative TMD within a protein. Overall, the library contained 6175 entries distinct at the sub-species/variants level. Entries belonging to the same taxonomic species were grouped into clusters which contained multiple sequences derived from several sub-species or variants. For our statistical analysis (Wilcoxon Rank Test) only clusters in which n>3 were used (overall 2874 entries were grouped into 265 clusters). Taxonomic clustering of results was conducted according to the tax ID lineage of each distinct entry. In the next step, a pairwise alignment of the TCRα CP (GLRILLLKV; SEQ ID NO: 37) was performed against each of the dataset sequences utilizing the EMBOSS package Needle pairwise global alignment (Needleman and Wunsch J. Mol. Biol. 48: 443-453, 1970) at the server (http://www.ebi.ac.uk/Tools/emboss/align/index.html). Alignments parameters were set using the Blosum40 matrix with gap opening/cost of 10/10 respectively. Results were ranked according to the clusters' Z-score (normalized by the mean and standard deviation of the 265 clusters alignment scores) (Pearson and Lipman, Proc. Natl. Acad. Sci. U.S.A. 85: 2444-2448, 1988) and were analyzed using Matlab software (MathWorks, Natick, Mass.). Statistical significance was determined according to the Benjamini-Hochberg method (E(FDR)<0.05) (Hochberg Y, Benjamini Y, Stat. Med. 9: 811-818, 1990).

Example 1

Bioinformatics Database Analysis

A peptide comprising nine amino acids (GLRILLLKV; SEQ ID NO: 37), derived from the TCRα transmembrane domain (TMD) (designated TCRα CP) was shown to interfere with TCR function (Manolios et al., 1997, Nat. Med. 3: 84-8). A TMD sequence library derived from a group of different viruses was constructed using the Uniport Knowledge Base, and compared to the TMD of TCRα using a systematic pairwise alignment (EMBOSS package: Needle global alignment; Needleman and Wunsch, J. Mol. Biol. 48: 443-453, 1970).

The results indicated that the top-ranked sequence belongs to the TMD of the Simian immunodeficiency virus (SIV) gp160 Envelope protein (FIG. 2A, Accession number: Q8AIH5). The SIV TMD (21 aa) contains a 9 amino acid sequence (GLRILMFIV; SEQ ID NO: 38) with 88.9% similarity and 66.7% identity to the TCRα CP. FIG. 2A demonstrates TCRα CP/SIV gp41 TMD sequence alignment. An additional top-ranked entry is the HIV-1 gp41 TM (Accession number: P03378). FIG. 2B demonstrates TCRα CP/HIV gp41 TMD sequence alignment.

Figure 2C:
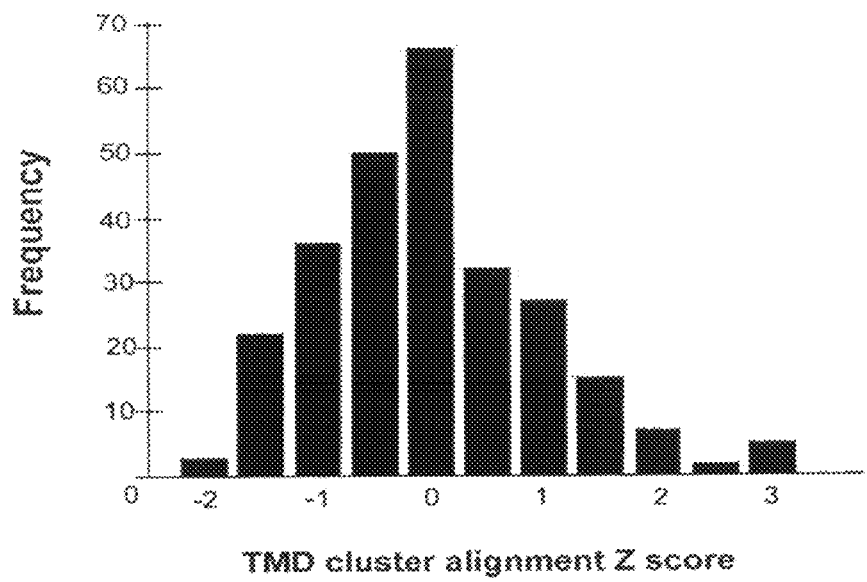
FIG. 2 demonstrates sequence alignment of TCRα CP, SIV gp41 TMD and HIV gp41 TMD.

All the sequence entries (n>3) belonging to a distinct species have been grouped into 265 TMD clusters (over all 2874 sequence entries), according to taxonomic species division. FIG. 2C displays the averaged normalized Z-score distribution of each cluster. Interestingly, the top-four ranked viral protein clusters were composed of the TMDs of HIV-1 gp160 (namely HIV-1 gp41), Feline immunodeficiency virus (FIV) gp150 and two TMDs within the latent membrane protein 1 (LMP1) from Epstein-Barr virus (EBV). Despite the fact that a single sequence entry within the SIV gp160 cluster (Accession number: Q8AIH5) was the top ranked alignment, the SIV gp160 cluster was ranked lower.

Figure 2D:
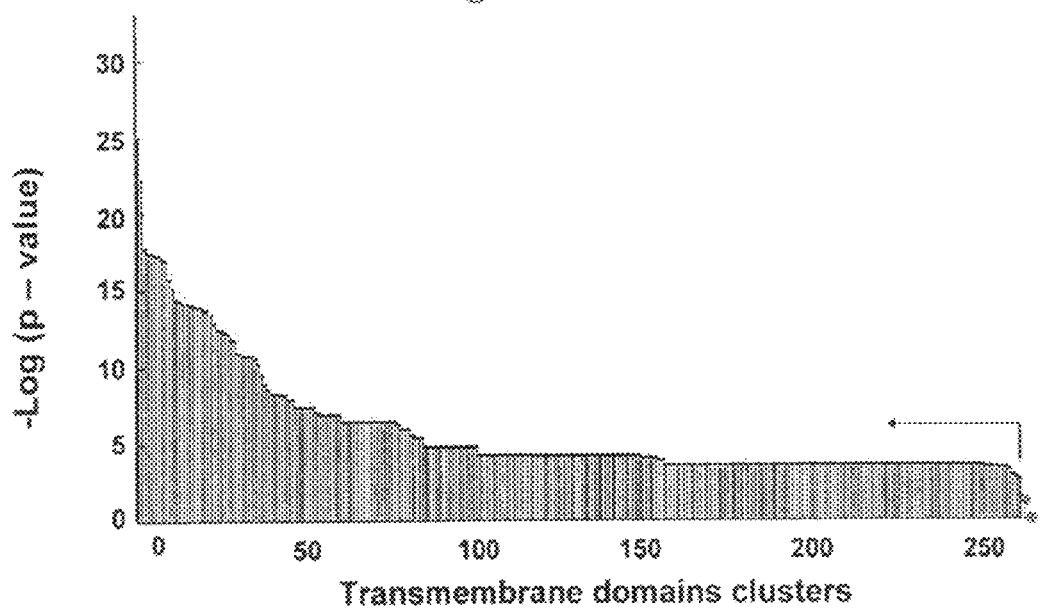

To statistically test the observation that HIV-1 gp41 TMD cluster was significantly ranked higher, a Wilcoxon Rank Test was performed. The HIV-1 gp41 TMD cluster (n=47) was compared against all the other 264 clusters using Wilcoxon Rank Test. P-value results of comparisons are present in a log scale. Significance of ranking was determined according to the Benjamin-Hochberg method. As shown in FIG. 2D, the HIV-1 gp41 TMD cluster was ranked significantly higher than all the other clusters that were not included within this top four group (FIV gp150 and EBV LMP1).

Example 2

Gp41 Transmembrane Domain (TMD) Distribution and Co-Localization with the CD3/TCR Complex in Resting and Activated T Cells It has been reported that the TCR, CD3, and CD4 receptors, among other components, are found in micro-domains in the membranes of activated CD4+ T cells. The localization and distribution of the CD3 molecules in the membrane of resting and activated T-cells was examined using Sy5 labeled antibodies designated to the CD3 molecule. The T cells had been activated by incubation with APC and the MOG 35-55 peptide. In resting T-cells, the CD3 molecules were found in micro-domains all around the T-cell, while the distribution of the CD3 molecules in activated T-cells resembled a capping shape (FIG. 3A).

In order to examine the distribution of the gp41 transmembrane peptide in the membrane of resting and activated mice T cells, gp41 TMD (KKKLFIMIVGGLVGLRIVFAVLSIKKK; SEQ ID NO: 10) was conjugated to the fluorescent probe 4-chloro-7-nitrobenz-2-oxa-1,3-diazole (NBD) (FIG. 3A; gp41 TMD). Rather than uniformly labeling the T-cell membrane, the gp41-TM showed a heterogeneous membrane distribution in the resting T cells and, unexpectedly, a capping shape on the membrane of activated T-cells. This distribution in membrane domains contrasted with that of a control membrane-active amphipathic peptide conjugated to NBD (FIG. 3A; AMP), which demonstrated a uniform distribution and no capping shape on activated T-cell membranes.

Figure 3A:
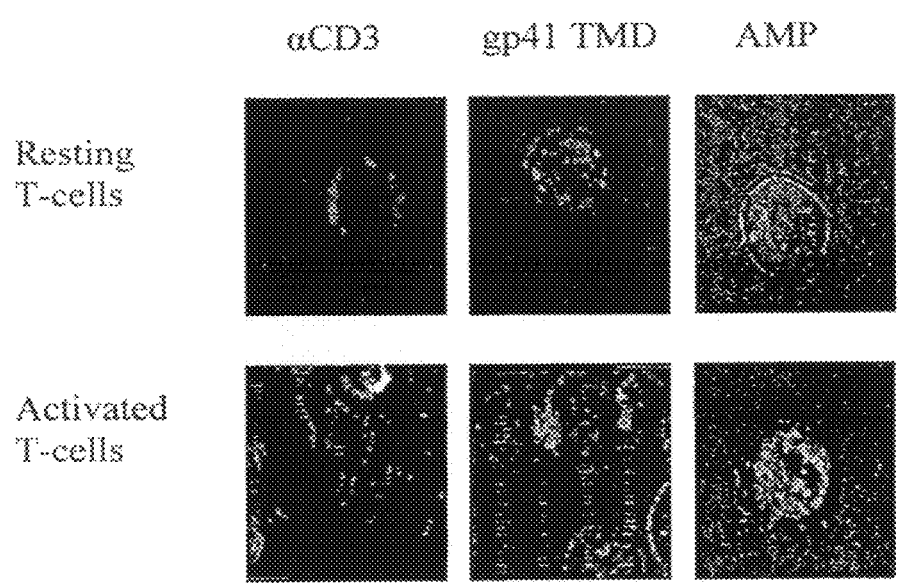
FIG. 3 demonstrates the co-localization of gp41 transmembrane domain (TMD) with the CD3/TCR complex in resting and activated T-cells. (A) Distribution of Gp41 TMD, AMP and CD3 molecules in resting and activated T cells. (B) Co-localization of Gp41 TMD with the CD3 molecules (C) Co-localization of AMP with the CD3 molecules.

FIG. 3A shows that in resting T cells, gp41 TMD peptides are heterogeneously distributed across the cell's membrane; whereas in activated T-cells, the gp41 TMD peptides demonstrate a capping shape distribution. Surprisingly, the CD3 molecules and gp41 TND share the same distribution pattern.

Figure 3B:
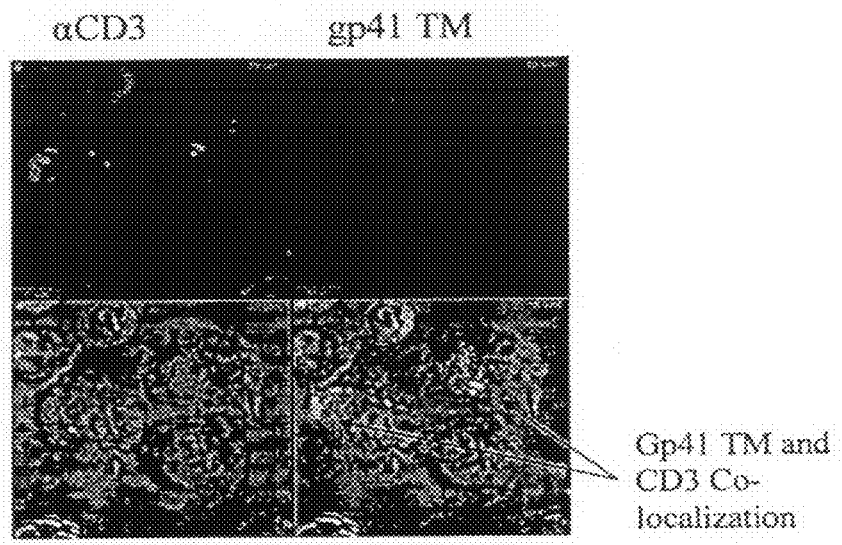
Figure 3C:
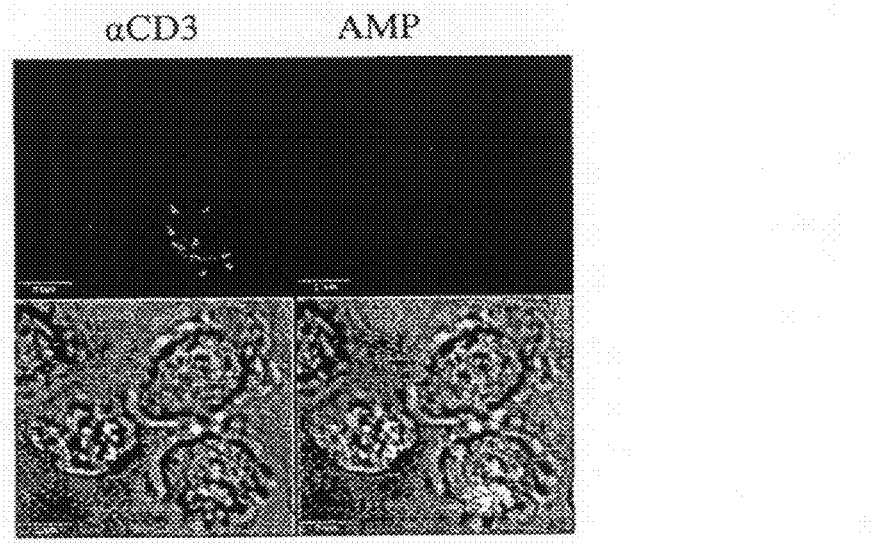

Further, it was demonstrated that the gp41 TMD peptide not only shares the same distribution pattern as CD3 but also co-localizes with the CD3 molecules (58.8%, FIG. 3B) compared to the AMP control peptide (27%, FIG. 3C).

FIG. 3B shows that the gp41 TMD peptide co-localizes with the CD3 within the TCR molecule.

Example 3

Effect of the gp41 Transmembrane Domain Peptide and a Peptide Derived Thereof ($TM_{11-19}$) on T-Cell Proliferation In Vitro The MOG 35-55 peptide is known to induce strong proliferative responses and cytokine release from T cells in the draining lymph node cells of MOG 35-55-immunized mice.

Figure 4A:
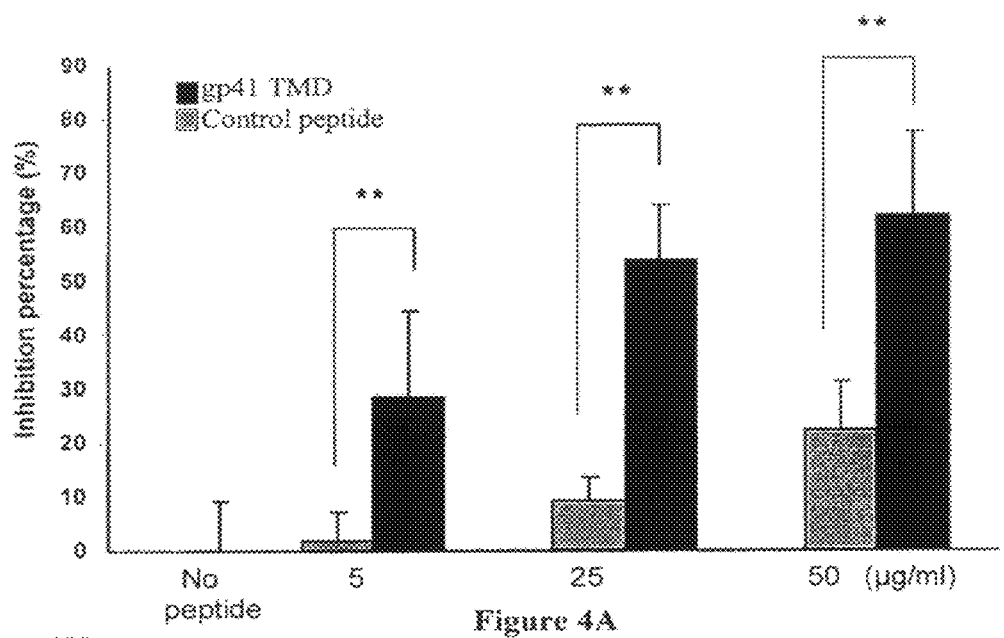
FIG. 4 shows the effect of gp41 TMD domain and gp41$_{11\text{-}19}$ on T-cell proliferation in vitro.
Figure 4B:
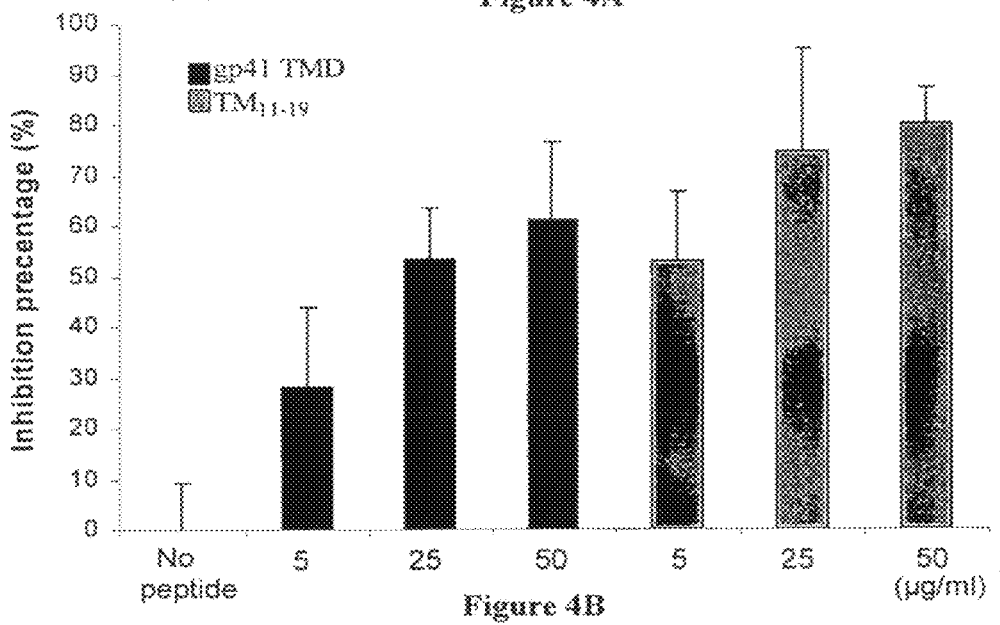

Lymph node cells were prepared from MOG 35-55/CFA immunized mice and their T cell response to the MOG 35-55 peptide was studied. T-cells were activated with the MOG 35-55 peptide and APC in the presence of gp41 TMD and $TM_{11-19}$ (GLVGLRIVF; SEQ ID NO: 6) in three different concentrations (5, 25 and 50 µg/ml) and the proliferative responses was assayed. The T cell line proliferative response was determined after 3 days of incubation using a H3-thymidine uptake assay. FIG. 4 shows a dose dependent inhibition caused by the two peptides. The uninhibited T-cell proliferative responses were 9382±891 cpm. Surprisingly, not only did the $TM_{11-19}$ peptide strongly inhibit T-cell proliferation, it exhibited better activity than the full length TMD peptide. The inhibitory effects of gp41 TMD and $TM_{11-19}$ on antigen-triggered proliferation was not due to cell death, because cells incubated with gp41 TMD and $TM_{11-19}$, or a control, in which PBS was added, showed the same survival in culture.

FIG. 4 shows that gp41 TMD and $TM_{11-19}$ peptides inhibit T-cell proliferation in vitro.

Example 4

Effect of the gp41 TMD and a Peptide Derived Thereof on T-Cell Activation Induced by Antibodies to CD3

To determine whether gp41 TMD can also inhibit T-cell activation other than that induced by APC presentation of specific antigen (e.g. MOG 35-55), T-cell activation was induced by a mitogenic monoclonal antibody specific to CD3. Mitogenic anti-CD3 antibodies activate CD3 signaling regardless of the presence or absence of TCR (Keppler et al., 2006, *J. Leukoc. Biol.* 79, 616-627). Thus, T-cells were activated with 1 µg/ml anti-CD3 and APC in the presence of 50 µg/ml gp41 TMD or gp41 $TM_{11-19}$, and the proliferative responses were assayed. The TCRα Core Peptide (GLRILLLKV; SEQ ID NO: 37; TCRα CP) served as a control peptide.

Figure 5:
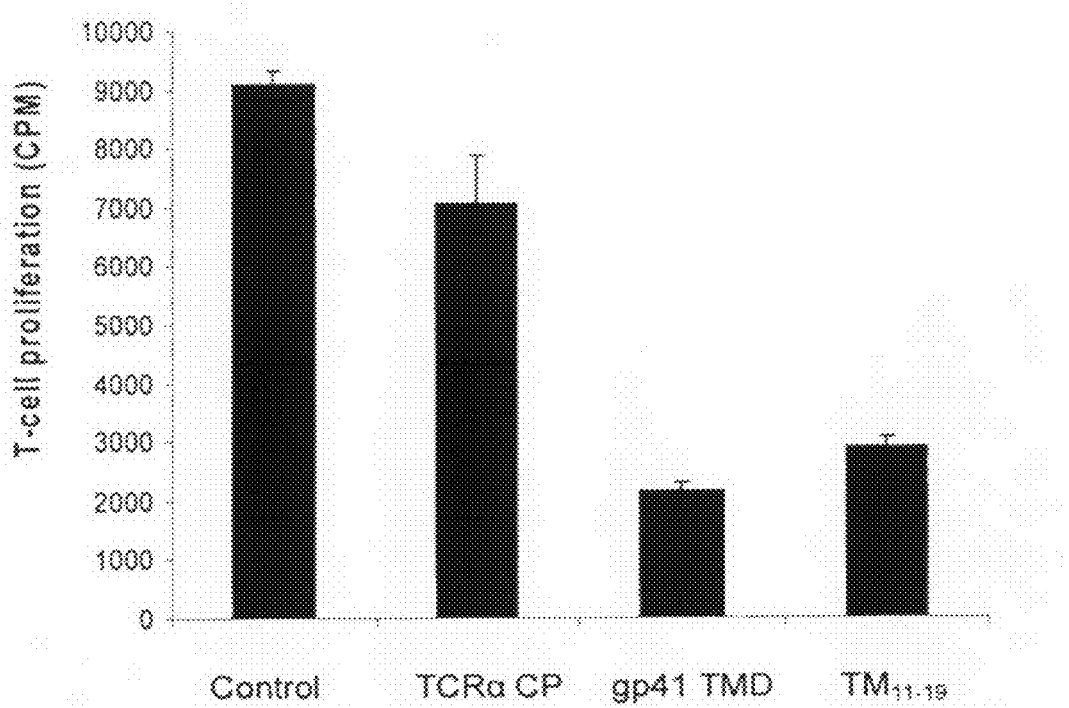
FIG. 5 shows the effect of gp41 TMD and gp41$_{11\text{-}19}$ on T-cell activation induced by antibodies to CD3.

Gp41 TMD and $TM_{11-19}$, unlike the full-length $FP_{1-33}$ (Quintana et al., 2005, *J. Clin. Invest.* 115, 2149-2158) or TCRα CP, inhibited the activation of T-cells by mitogenic anti-CD3 antibodies (FIG. 5). This further indicates that gp41 TMD interacts with the CD3 molecule.

FIG. 5 shows that gp41 TMD and a fragment thereof inhibit T-cell activation induced by antibodies to CD3.

Example 5

Effect of gp41 TMD and $gp41_{11-19}$ on T-Cell Activation Induced by PMA/Ionomycin To learn whether gp41 TMD can also inhibit T cell activation other than that induced by APC presentation of specific antigen or mitogenic monoclonal antibody to CD3 (of the TCR complex), the effect of gp41 TMD on T cell activation induced by PMA/ionomycin was tested. PMA/ionomycin activates the T cell downstream of the membrane regardless of the presence or absence of the TCR.

Gp41 TMD, like the TCRα CP, did not inhibit the activation of T cells by PMA/ionomycin, suggesting that gp41 TMD inhibits T cell activation by interfering with TCR and CD3 proper function.

Figure 6:
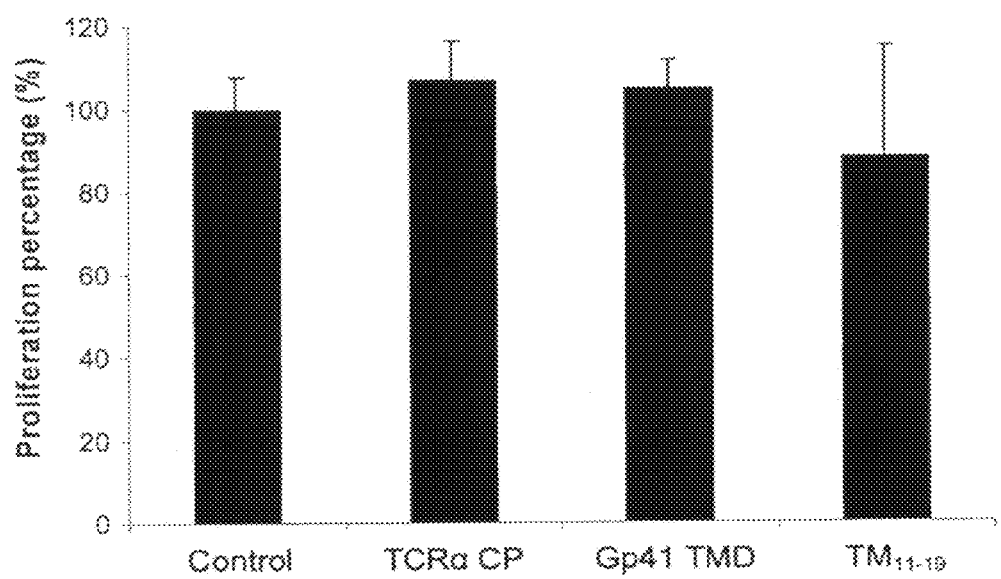
FIG. 6 shows the effect of gp41 TMD and gp41$_{11\text{-}19}$ on T-cell activation induced by PMA/ionomycin.

FIG. 6 shows that Gp41 TMD does not inhibit T-Cell activation induced by PMA/ionomycin.

Example 6

Figure 7A:
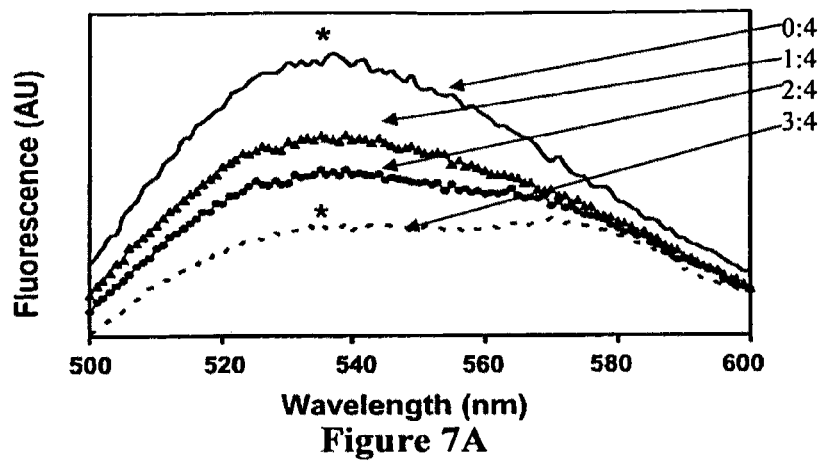
FIG. 7 depicts fluorescence energy transfer (FRET) measurement revealing the specific interaction between the gp41 TMD and the TCRα CP peptide.
Figure 7B:
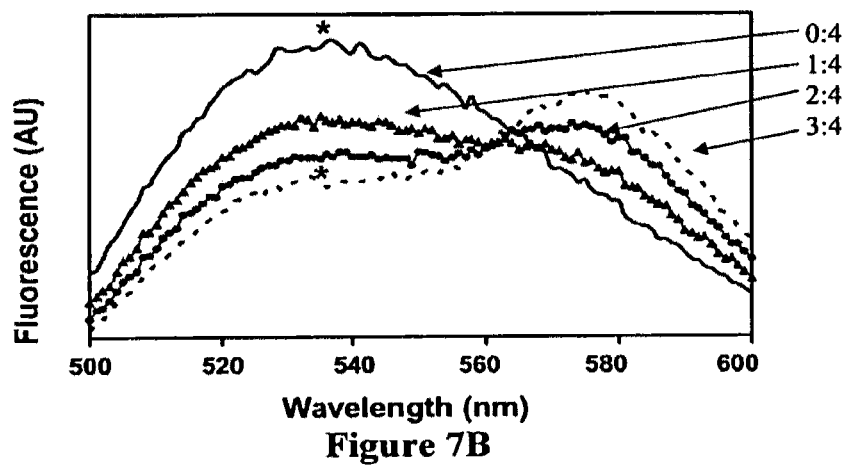
Figure 7C:
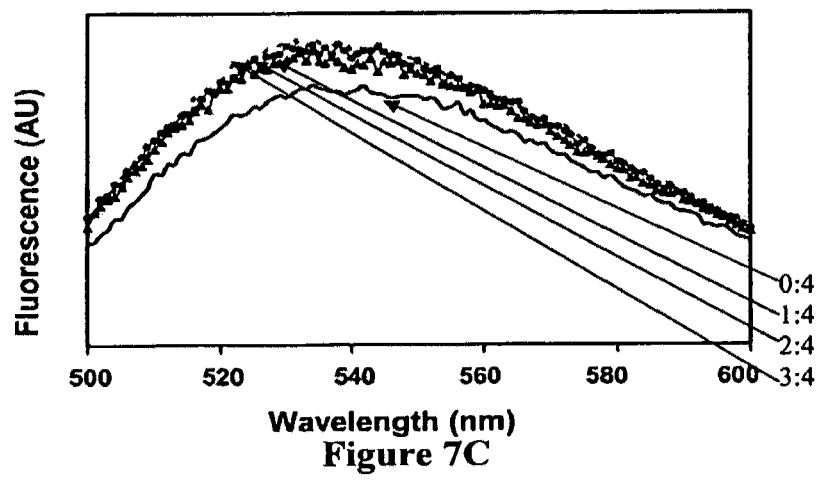

Fluorescence Energy Transfer (FRET) Measurements of the gp41 TMD and the TCRα CP Interaction Further investigations were performed to reveal whether gp41 TMD interacts solely with CD3 or perhaps it interacts with the TCRα TMD. TCRα CP peptide was labeled with NBD, as a donor fluorophore, and the gp41 TMD (FIG. 7A) and the TCRα CP (FIG. 7B) peptides with Rho-TAMRA, as an acceptor fluorophore. As a control hydrophobic peptide, an unrelated transmembrane peptide derived from the *E. coli* aspartate receptor (TAR/PS) was labeled as well (FIG. 7C). Then, the fluorescence energy transfer (FRET) was measured between fluorescently labeled TCRα CP-NBD peptide and gp41 TM-Rho, TCRα CP-Rho or TAR/PS-Rho. The assay was performed in a model lipid environment of large unilamellar vesicles (LUV) composed of PC lipid and in an isolated in vitro system. The Rho labeled peptides were added in four different ratios (0:4—black line, 1:4—black triangle, 1:2—black circle, and 3:4—dashed line). The TCRα CP-NBD peptide showed about ~50% energy transfer in the presence of the gp41 TM-Rho peptide at an acceptor-to-lipid ratio of 1:1000 (FIG. 7), indicating an interaction between the two peptides. When examining the energy transfer of TCRα CP-NBD peptide in the presence of TCRα CP-Rho peptide, a lower energy transfer percentage of ~37% was demonstrated. The TAR/PS-Rho control peptide did not show energy transfer.

Example 6 shows a specific interaction between the gp41 TMD and the TCRα CP peptide.

Example 7

Figure 8:
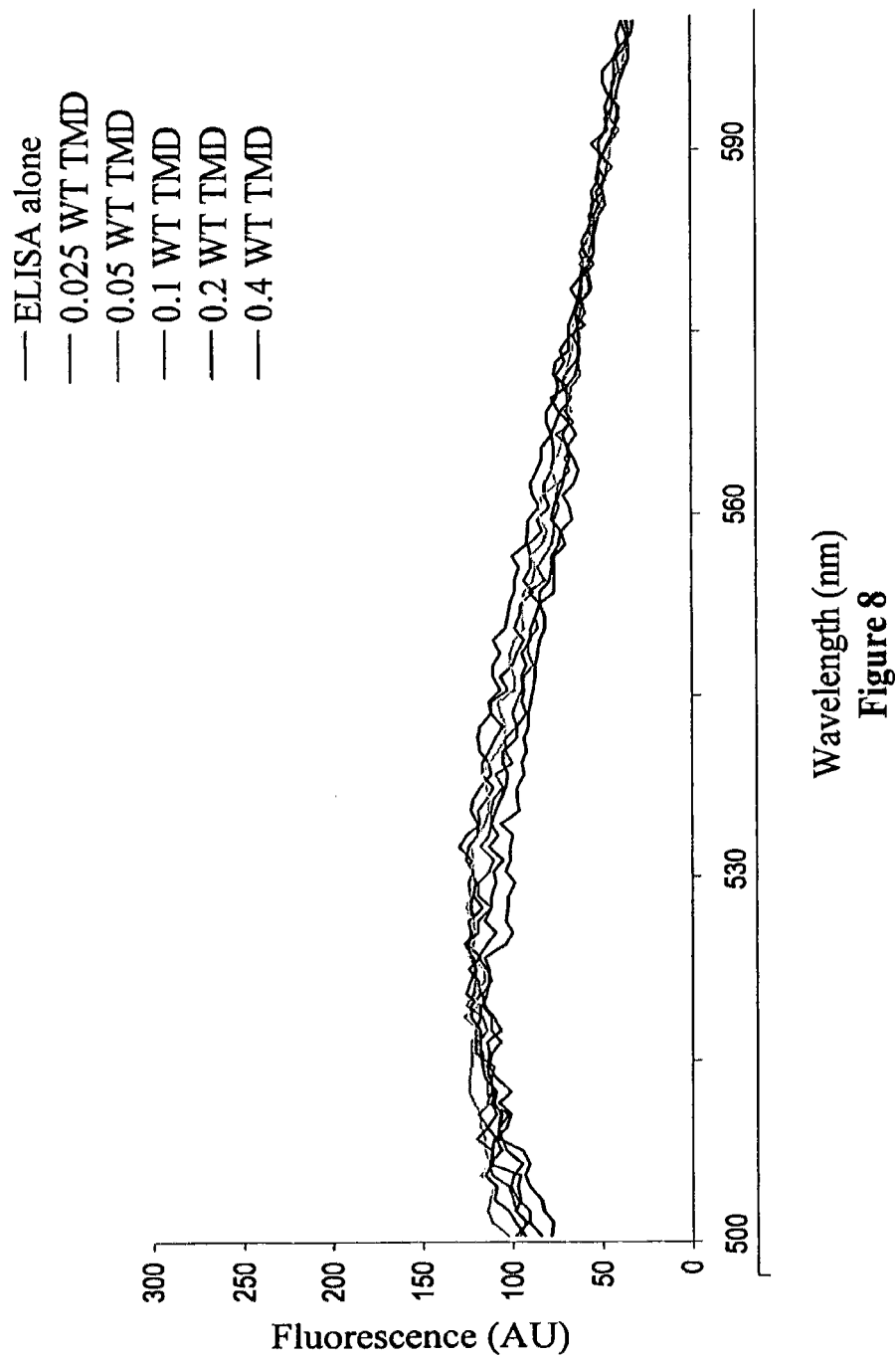
FIG. 8 depicts FRET measurement revealing the specific interaction between gp41 and TLR2 through their membrane spanning domains.
Figure 9:
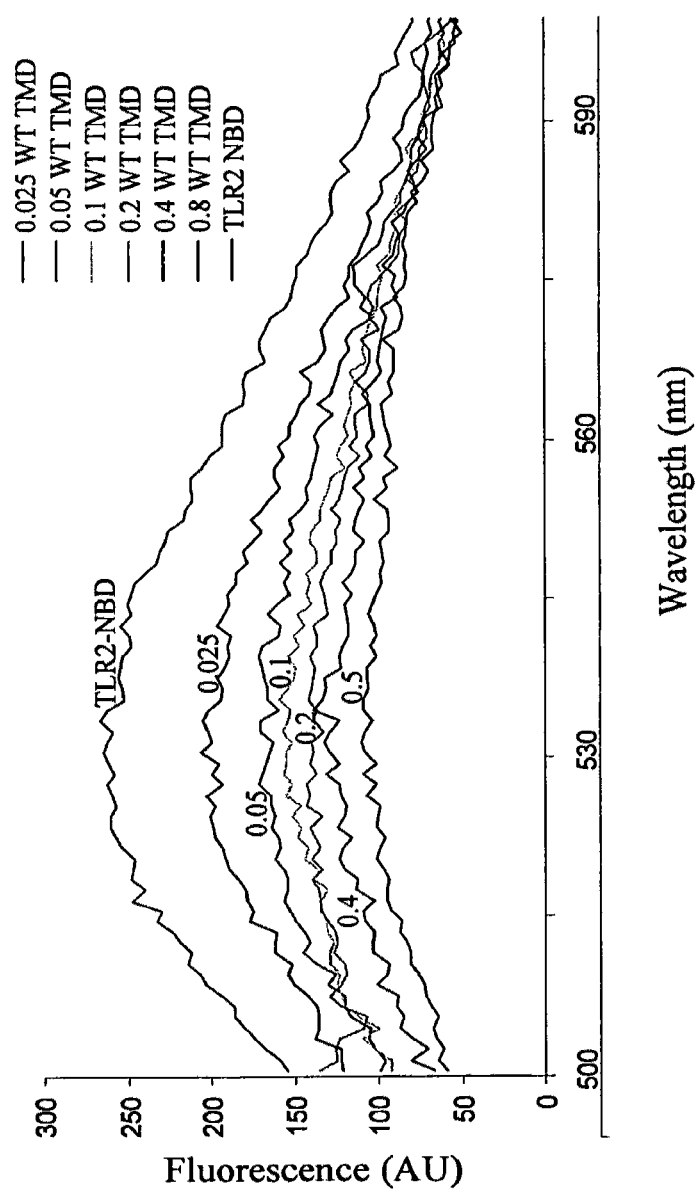
FIG. 9 depicts FRET measurement between TLR2 and TAR1p/s as a control.

Fluorescence Energy Transfer (FRET) Measurements of the gp41 TMD and the TLR2 Interaction The energy transfer from the association of the gp41 TMD and the TLR2 TMD peptides was measured in the presence of 100 µM LUVs. Gp41 TMD peptide was labeled with NBD and TLR2 was labeled with Rho. The concentration of the gp41 peptide was constant (0.4 µM) and continues amounts of TLR2—Rho were added (0.025 µM, 0.05 µM, 0.1 µM, 0.2 µM, 0.4 µM and 0.8 µM TLR2-Rho). As a control, the energy transfer between TLR2 and TAR1p/s (MVLGVFALL PLISGSL; SEQ ID NO:39) was measured. The concentration of the TAR1p/s peptide was constant (0.4 μM) and continues amounts of TLR2—Rho were added (0.025 μM, 0.05 μM, 0.1 μM, 0.2 μM and 0.4 μM TLR2—Rho). While with the TAR1p/s peptide no energy transfer was detected (FIG. 8), the percent of energy transfer between gp41 and TLR2 was over 60% (FIG. 9).

Example 7 shows that Gp41 and TLR2 associate through their membrane spanning domains.

Example 8

The effect of GP41 TMD peptide on TNFα secretion from RAW 264.7

Figure 10:
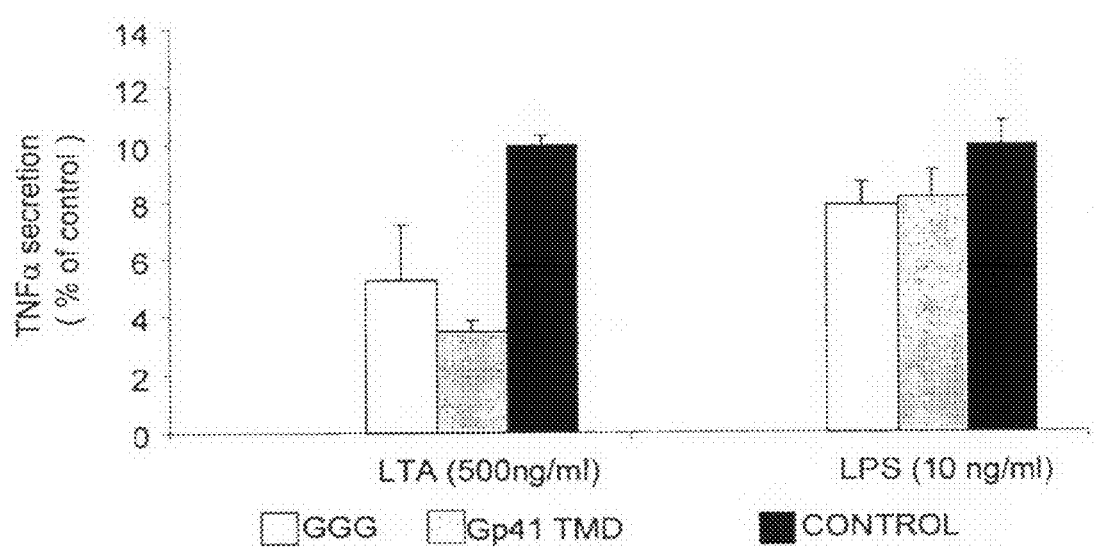
FIG. 10 shows gp41 TMD's effect on TNFα secretion from macrophages.

RAW264.7 macrophages were grown in the presence of gp41 TMD peptides for 2 hours at a concentration of 20 μM. As controls, RAW264.7 macrophages were grown in the presence of GGG peptides or in the absence of peptides (FIG. 10, GGG and Control, respectively). Thereafter, the medium was washed twice and 500 ng/ml of LTA or 10 ng/ml of LPS was added for 5 hours. In order to evaluate TNFα levels an ELISA assay was performed. Results are shown normalized to the level of TNFα secretion induced by the ligands in the absence of peptides (FIG. 10 Control). The result is an average of three measurements.

FIG. 10 shows that the gp41 TMD peptide inhibits TNFα secretion from macrophages in response to activation with LTA and reduces TNFα secretion in response to activation with LPS.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An isolated peptide of 10-30 amino acids, or an analog thereof, comprising the amino acid sequence of general formula I:

```
                                            (SEQ ID NO: 1)
    Gly-X1-X2-X3-Leu-X4-Ile-Val-Phe,
``` wherein $X_1$ is selected from the group consisting of a Leucine (Leu) and a Glycine (Gly) amino acid residue;

$X_2$ is selected from the group consisting of a Valine (Val) and a Leucine (Leu) amino acid residue;

$X_3$ is selected from the group consisting of a Glycine (Gly) and a Valine (Val) amino acid residue; and $X_4$ is selected from the group consisting of an Arginine (Arg) and a Glutamic acid (Glu) amino acid residue; further comprising 1-4 basic amino acid residues contiguous to at least one termini of the amino acid sequence, wherein the analog comprises one or more D-amino acids.

2. The isolated peptide of claim 1, wherein $X_1$ is a Leucine, $X_2$ is a Valine and $X_3$ is a Glycine residue, or wherein $X_1$ is a Glycine, $X_2$ is a Leucine, $X_3$ is a Valine and $X_4$ is an Arginine residue.

3. The isolated peptide of claim 2, wherein the amino acid sequence is selected from the group consisting of:

```
                                            (SEQ ID NO: 6)
    GLVGLRIVF, (SEQ ID NO: 4)
    IVGGLVGLRIVFAV, (SEQ ID NO: 3)
    IVGGLVGLRIVFAVL, (SEQ ID NO: 2)
    LFIMIVGGLVGLRIVFAVLSIV, (SEQ ID NO: 5)
    IVGGLVELRIVFAV,
    and (SEQ ID NO: 7)
    IVGGGLVLRIVFAV.
```

4. The isolated peptide of claim 1, wherein the basic amino acid residue is selected from Lysine and Arginine residues.

5. The isolated peptide of claim 4, consisting of the amino acid sequence KKKLFIMIVGGLVGLRIVFAVLSIKKK (SEQ ID NO: 10).

6. A lipophilic conjugate comprising an isolated peptide according claim 1, conjugated to a hydrophobic moiety.

7. The lipophilic conjugate according to claim 6, wherein the hydrophobic moiety is selected from the group consisting of a fatty acid, a sterol and a vitamin.

8. The lipophilic conjugate according to claim 7, wherein the fatty acid has at least six carbon atoms.

9. The lipophilic conjugate according to claim 8, wherein the fatty acid is selected from the group consisting of: octanoic acid, decanoic acid, undecanoic acid, dodecanoic acid, myristic acid, palmitic acid, stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, and cerebronic acid.

10. A pharmaceutical composition comprising as an active ingredient an isolated peptide according to claim 1, and a pharmaceutically acceptable carrier.

11. A pharmaceutical composition comprising as an active ingredient a lipophilic conjugate of claim 6, and a pharmaceutically acceptable carrier.

12. The lipophilic conjugate according to claim 6, wherein the hydrophobic moiety is conjugated to the N-terminus or C-terminus of said isolated peptide.

13. The lipophilic conjugate according to claim 9, wherein the fatty acid is selected from the group consisting of: undecanoic acid, octanoic acid and myristic acid.

* * * * *